(12) United States Patent
Michaelides et al.

(10) Patent No.: US 8,293,738 B2
(45) Date of Patent: Oct. 23, 2012

(54) INDAZOLE INHIBITORS OF KINASE

(75) Inventors: Michael R. Michaelides, Libertyville, IL (US); James H. Holms, Gurnee, IL (US); Douglas H. Steinman, Morton Grove, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/106,189

(22) Filed: May 12, 2011

(65) Prior Publication Data
US 2011/0281868 A1    Nov. 17, 2011

Related U.S. Application Data

(60) Provisional application No. 61/333,843, filed on May 12, 2010.

(51) Int. Cl.
| | |
|---|---|
| A61K 31/5375 | (2006.01) |
| A61K 31/445 | (2006.01) |
| A61K 31/425 | (2006.01) |
| A61K 31/42 | (2006.01) |
| A61K 31/416 | (2006.01) |
| A61K 31/4155 | (2006.01) |
| C07D 413/14 | (2006.01) |
| C07D 401/14 | (2006.01) |
| C07D 277/20 | (2006.01) |
| C07D 261/06 | (2006.01) |
| C07D 403/14 | (2006.01) |
| C07D 231/56 | (2006.01) |

(52) U.S. Cl. ............ 514/234.5; 514/322; 514/365; 514/338; 514/378; 514/403; 514/406; 544/140; 546/199; 546/275.7; 548/202; 548/247; 548/255; 548/361.1

(58) Field of Classification Search .......... 514/234.5, 514/322, 365, 338, 378, 403, 406; 544/140; 546/199, 275.7; 548/202, 247, 255, 361.1
See application file for complete search history.

(56) References Cited

U.S. PATENT DOCUMENTS

| | | | |
|---|---|---|---|
| 4,831,031 | A | 5/1989 | Lowe, III |
| 5,041,453 | A | 8/1991 | Huang et al. |
| 5,140,034 | A | 8/1992 | Baker et al. |
| 5,206,366 | A | 4/1993 | Bowles |
| 5,208,236 | A | 5/1993 | Neustadt |
| 5,270,148 | A | 12/1993 | Morigaki et al. |
| 5,415,990 | A | 5/1995 | Kaneko et al. |
| 5,495,024 | A | 2/1996 | Itoh et al. |
| 5,532,240 | A | 7/1996 | Nakao et al. |
| 5,616,537 | A | 4/1997 | Yokota et al. |
| 5,922,733 | A | 7/1999 | Forbes et al. |
| 5,929,250 | A | 7/1999 | Widdowson et al. |
| 6,166,027 | A | 12/2000 | Straub et al. |
| 6,242,470 | B1 | 6/2001 | Baxter et al. |
| 6,391,872 | B1 | 5/2002 | Marfat |
| 6,395,749 | B1 | 5/2002 | Li et al. |
| 2001/0003121 | A1 | 6/2001 | Baxter et al. |
| 2002/0039767 | A1 | 4/2002 | Maier |
| 2002/0058687 | A1 | 5/2002 | Marfat |
| 2002/0198213 | A1 | 12/2002 | Zhou et al. |
| 2003/0055097 | A1 | 3/2003 | Zhang et al. |
| 2003/0069278 | A1 | 4/2003 | Zhou et al. |
| 2003/0078286 | A1 | 4/2003 | Li et al. |
| 2003/0176424 | A1 | 9/2003 | He et al. |
| 2004/0034229 | A1 | 2/2004 | Taveras et al. |
| 2004/0054180 | A1 | 3/2004 | Zhang et al. |
| 2004/0092546 | A1 | 5/2004 | Wei et al. |
| 2004/0097547 | A1 | 5/2004 | Taveras et al. |
| 2004/0132790 | A1 | 7/2004 | Xie et al. |
| 2004/0171634 | A1 | 9/2004 | Kania et al. |
| 2004/0236101 | A1 | 11/2004 | Makriyannis et al. |
| 2004/0248853 | A1 | 12/2004 | Dyckman et al. |
| 2005/0009894 | A1 | 1/2005 | Babin et al. |
| 2005/0014764 | A1 | 1/2005 | Romano et al. |
| 2005/0026969 | A1 | 2/2005 | Cheng et al. |
| 2005/0038097 | A1 | 2/2005 | Bender et al. |
| 2005/0054697 | A1 | 3/2005 | Yager et al. |
| 2005/0113283 | A1 | 5/2005 | Solow-Cordero et al. |
| 2005/0197340 | A1 | 9/2005 | Arora et al. |
| 2005/0234095 | A1 | 10/2005 | Xie et al. |
| 2005/0261298 | A1 | 11/2005 | Solow-Cordero et al. |
| 2005/0272735 | A1 | 12/2005 | Xie et al. |
| 2005/0282809 | A1 | 12/2005 | Ono et al. |

(Continued)

FOREIGN PATENT DOCUMENTS

EP    0562832 A1    9/1993

(Continued)

OTHER PUBLICATIONS

International Search Report and Written Opinion for Application No. PCT/US2011/036250, mailed on Oct. 31, 2011, 10 pages.
Araki K., et al., "High Expression of Aurora-B/Aurora and Ipl1-Like Midbody-Associated Protein (AIM-1) in Astrocytomas," Journal of Neuro-Oncology, 2004, vol. 67 (1-2), pp. 53-64.
Bischoff J.R., et al., "A Homologue of *Drosophila* Aurora Kinase is Oncogenic and Amplified in Human Colorectal Cancers," The EMBO Journal, 1998, vol. 17 (11), pp. 3052-3065.

(Continued)

*Primary Examiner* — Joseph K. McKane
*Assistant Examiner* — Samantha Shterengarts
(74) *Attorney, Agent, or Firm* — Susan L. Steele

(57) ABSTRACT

The present invention relates to compounds of formula (I) or pharmaceutical acceptable salts,

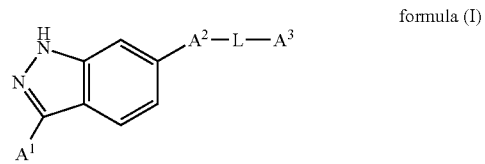

formula (I)

wherein $A^1$, $A^2$, $A^3$ and L are defined in the description. The present invention relates also to methods of making said compounds, and compositions containing said compounds which are useful for inhibiting kinases such as aurora and KDR.

23 Claims, No Drawings

U.S. PATENT DOCUMENTS

| | | |
|---|---|---|
| 2006/0135589 A1 | 6/2006 | Berdino et al. |
| 2006/0142317 A1 | 6/2006 | Bakker et al. |
| 2007/0015809 A1 | 1/2007 | Bressi et al. |
| 2007/0032515 A1 | 2/2007 | Anand et al. |
| 2007/0054942 A1 | 3/2007 | Patel et al. |
| 2007/0129404 A1 | 6/2007 | Hagihara et al. |
| 2007/0142372 A1 | 6/2007 | Campos et al. |
| 2007/0238877 A1 | 10/2007 | Tyagi et al. |
| 2007/0249614 A1 | 10/2007 | Brown et al. |
| 2007/0282101 A1 | 12/2007 | Ericsson et al. |
| 2008/0003656 A1 | 1/2008 | Loffert et al. |
| 2008/0004539 A1 | 1/2008 | Ross |

FOREIGN PATENT DOCUMENTS

| | | |
|---|---|---|
| EP | 1040829 A2 | 10/2000 |
| JP | 8225535 A | 9/1996 |
| JP | 2001011047 A | 1/2001 |
| JP | 3245765 B2 | 1/2002 |
| JP | 2007016011 A | 1/2007 |
| WO | WO9748786 A1 | 12/1997 |
| WO | WO0021954 A1 | 4/2000 |
| WO | WO0027627 A1 | 5/2000 |
| WO | WO0042045 A2 | 7/2000 |
| WO | WO0236562 A2 | 5/2002 |
| WO | WO02076926 A1 | 10/2002 |
| WO | WO02083624 A1 | 10/2002 |
| WO | WO2004069828 A1 | 8/2004 |
| WO | WO2005014554 A1 | 2/2005 |
| WO | WO2005044181 A2 | 5/2005 |
| WO | WO2005073189 A1 | 8/2005 |
| WO | WO2005073219 A1 | 8/2005 |
| WO | WO2005094823 A1 | 10/2005 |
| WO | WO2006069809 A1 | 7/2006 |
| WO | WO2006081562 A2 | 8/2006 |
| WO | WO2006105865 A1 | 10/2006 |
| WO | WO2006129158 A2 | 12/2006 |
| WO | WO2007015866 A2 | 2/2007 |
| WO | WO2007029077 A1 | 3/2007 |
| WO | WO2007058626 A1 | 5/2007 |
| WO | WO2007075847 A2 | 7/2007 |
| WO | WO2007092751 A2 | 8/2007 |
| WO | WO2007099374 A1 | 9/2007 |
| WO | WO2007114763 A1 | 10/2007 |
| WO | WO2007117995 A2 | 10/2007 |
| WO | WO2007126841 A2 | 11/2007 |
| WO | WO2007135380 A2 | 11/2007 |
| WO | WO2007142323 A1 | 12/2007 |
| WO | WO2010007114 A2 | 1/2010 |
| WO | WO2010007116 A2 | 1/2010 |

OTHER PUBLICATIONS

Bodvarsdottir S.K., et al., "Aurora-A Amplification Associated With BRCA2 Mutation in Breast Tumours," Cancer Letter, 2007, vol. 248 (1), pp. 96-102.

Chen J., et al., "Association Between Aurora-A Kinase Polymorphisms and Age of Onset of Hereditary Nonpolyposis Colorectal Cancer in a Caucasian Population," Molecular Carcinogenesis, 2007, vol. 46 (4), pp. 249-256.

Chieffi P., et al., "Aurora B Expression Directly Correlates With Prostate Cancer Malignancy and Influence Prostate Cell Proliferation," Prostate, 2006, vol. 66 (3), pp. 326-333.

Comperat E., et al., "Aurora-A/STK-15 is a Predictive Factor for Recurrent Behaviour in Non-Invasive Bladder Carcinoma: A Study of 128 Cases of Non-Invasive Neoplasms," Virchows Archiv., 2007, vol. 450 (4), pp. 419-424.

Cox D.G., et al., "Polymorphisms of the AURKA (STK15/Aurora Kinase) Gene and Breast Cancer Risk," Cancer Causes Control, 2006, vol. 17 (1), pp. 81-83.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.

Ellis L.M., et al, "VEGF-Targeted Therapy Mechanisms of Anti-Tumour Activity," Nature Reviews Cancer, 2008, vol. 8 (8), pp. 579-591.

Ewart T.A., et al., "Aurora-A/STK15 T+91A is a General Low Penetrance Cancer Susceptibility Gene: A Meta-Analysis of Multiple Cancer Types," Carcinogenesis, 2005, vol. 26 (8), pp. 1368-1373.

Ewart-Toland A., et al., "Identification of Stk6/STK15 as a Candidate Low-Penetrance Tumor-Susceptibility Gene in Mouse and Human," Nature Genetics, 2003, vol. 34 (4), pp. 403-412.

Fraizer G.C., et al., "Aurora-A/STK15/BTAK Enhances Chromosomal Instability in Bladder Cancer Cells," International Journal of Oncology, 2004, vol. 25 (6), pp. 1631-1639.

Gu J., et al., "Polymorphisms of STK15 (Aurora-A) Gene and Lung Cancer Risk in Caucasians," Carcinogenesis, 2007, vol. 28 (2), pp. 350-355.

Hienonen T., et al., "Preferential Amplification of Aurka 91A (Ile31) in Familial Colorectal Cancers," International Journal of Cancer, 2006, vol. 118 (2), pp. 505-508.

Hoque A., et al., "Loss of Aurora A/STK15/BTAK Overexpression Correlates With Transition of in Situ to Invasive Ductal Carcinoma of the Breast," Cancer Epidemiology, Biomarkers and Prevention, 2003, vol. 12 (2), pp. 1518-1522.

Jeng Y.M., et al., "Overexpression and Amplification of Aurora-A in Hepatocellular Carcinoma," Clinical Cancer Research, 2004, vol. 10 (6), pp. 2065-2071.

Ju H., et al., "Functional Polymorphism 57Val>lle of Aurora Kinase A Associated With Increased Risk of Gastric Cancer Progression," Cancer Letter, 2006, vol. 242 (2), pp. 273-279.

Kimura M.T., et al., "Two Functional Coding Single Nucleotide Polymorphisms in STK15 (Aurora-A) Coordinately Increase Esophageal Cancer Risk," Cancer Research, 2005, vol. 65 (9), pp. 3548-3554.

Klein A., et al., "Overexpression and Amplification of STK15 in Human Gliomas," International Journal of Oncology, 2004, vol. 25 (6), pp. 1789-1794.

Kolb A.J., et al., "Tyrosine Kinase Assays Adapted to Homogeneous Time-Resolved Fluorescence," Drug Discovery Today, 1998, vol. 3 (7), pp. 333-342.

Kurahashi T., et al., "Significance of Aurora-A Expression in Renal Cell Carcinoma," Urologic Oncology, 2007, vol. 25 (2), pp. 128-133.

Landen C.N., et al, "Overexpression of the Centrosomal Protein Aurora-A Kinase is Associated With Poor Prognosis in Epithelial Ovarian Cancer Patients," Clinical Cancer Research, 2007, vol. 13 (14), pp. 4098-4104.

Lassmann S., et al., "Predictive Value of Aurora-A/STK15 Expression for Late Stage Epithelial Ovarian Cancer Patients Treated by Adjuvant Chemotherapy," Clinical Cancer Research, 2007, vol. 13 (14), pp. 4083-4091.

Li F.C., et al., "Deletion of P15 and P16 Genes and Overexpression of STK15 Gene in Human Laryngeal Squamous Cell Carcinoma," National Medical Journal of China, 2003, vol. 83 (4), pp. 316-319.

Lin Y.S., et al, "Gene Expression Profiles of the Aurora Family Kinases," Gene Expression, 2006, vol. 13(1), pp. 15-26.

Lo Y.L., et al., "Breast Cancer Risk Associated With Genotypic Polymorphism of the Mitosis-Regulating Gene Aurora-A/STK15/BTAK," International Journal of Cancer, 2005, vol. 115 (2), pp. 276-283.

Mathis G., "HTRF(R) Technology," Journal of Biomolecular Screening, 1999, vol. 4 (6), pp. 309-314.

Miyoshi Y., et al., "Association of Centrosomal Kinase STK15/BTAK mRNA Expression With Chromosomal Instability in Human Breast Cancers," International Journal of Cancer, 2001, vol. 92 (3), pp. 370-373.

Moreno B.G., et al., "Differential Gene Expression Profile in Endometrioid and Nonendometrioid Endometrial Carcinoma: STK15 is Frequently Overexpressed and Amplified in Nonendometrioid Carcinomas," Cancer Research, 2003, vol. 63 (18), pp. 5697-5702.

Neben K., et al., "Microarray-Based Screening for Molecular Markers in Medulloblastoma Revealed STK15 as Independent Predictor for Survival," Cancer Research, 2004, vol. 64 (9), pp. 3103-3111.

Nishida N., et al., "High Copy Amplification of the Aurora-A Gene is Associated With Chromosomal Instability Phenotype in Human Colorectal Cancers," Cancer Biology and Therapy, 2007, vol. 6 (4), pp. 525-533.

Qi G., et al., "Aurora-B Expression and its Correlation With Cell Proliferation and Metastasis in Oral Cancer," Virchows Arch., 2007, vol. 450 (3), pp. 297-302.

Reichardt W., et al., "The Putative Serine/Threonine Kinase Gene STK15 on Chromosome 20q13.2 is Amplified in Human Gliomas," Molecular Endocrinology, 2003, vol. 10 (5), pp. 1275-1279.

Reiter R., et al., "Aurora Kinase a Messenger RNA Overexpression is Correlated With Tumor Progression and Shortened Survival in Head and Neck Squamous Cell Carcinoma," Clinical cancer Research, 2006, vol. 12 (17), pp. 5136-5141.

Royce M.E., et al., "STK15/Aurora-A Expression in Primary Breast Tumors is Correlated With Nuclear Grade but Not With Prognosis," Cancer, 2004, vol. 100 (1), pp. 12-19.

Sen S., et al., "A Putative Serine/Threonine Kinase Encoding Gene BTAK on Chromosome 20q13 is Amplified and Overexpressed in Human Breast Cancer Cell Lines," Oncogene, 1997, vol. 14 (18), pp. 2195-2200.

Sen S., et al., "Amplification/Overexpression of a Mitotic Kinase Gene in Human Bladder Cancer," Journal of the National Cancer Institute, 2002, vol. 94 (17), pp. 1320-1329.

Smith S.L., et al., "Overexpression of Aurora B Kinase (AURKB) in Primary Non-Small Cell Lung Carcinoma is Frequent, Generally Driven From One Allele, and Correlates With the Level of Genetic Instability," British Journal of Cancer, 2005, vol. 93 (6), pp. 719-729.

Sorrentino R., et al., "Aurora B Overexpression Associates With the Thyroid Carcinoma Undifferentiated Phenotype and is Required for Thyroid Carcinoma Cell Proliferation," The Journal of Clinical Endocrinology and Metabolism, 2005, vol. 90 (2), pp. 928-935.

Sutton, V.R. et al., "Bcl-2 Prevents Apoptosis Induced by Perforin and Granzyme B, but Not That Mediated by Whole Cytotoxic Lymphocytes," Journal of Immunology, 1997, vol. 158 (12), pp. 5783-5790.

Tanaka T., et al., "Centrosomal Kinase AIK1 is Overexpressed in Invasive Ductal Carcinoma of the Breast," Cancer Research, 1999, vol. 59 (9), pp. 2041-2044.

Tatsuka M., et al., "Overexpression of Aurora-A potentiates HRAS-mediated Oncogenic Transformation and is Implicated in Oral Carcinogenesis," Oncogene, 2005, vol. 24 (6), pp. 1122-1127.

Tchatchou S., et al., "Aurora Kinases A and B and Familial Breast Cancer Risk," Cancer Letters, 2007, vol. 247 (2), pp. 266-272.

Tong T., et al., "Overexpression of Aurora-A Contributes to Malignant Development of Human Esophageal Squamous Cell Carcinoma," Clinical Cancer Research, 2004, vol. 10 (21), pp. 7304-7310.

Vidarsdottir L., et al., "Breast Cancer Risk Associated With AURKA 91T → A Polymorphism in Relation to BRCA Mutations," Cancer Letter, 2007, vol. 250 (2), pp. 206-212.

Vischioni B., et al., "Frequent Overexpression of Aurora B Kinase, a Novel Drug Target, in Non-Small Cell Lung Carcinoma Patients," Molecular cancer Therapeutics, 2006, vol. 5 (11), pp. 2905-2913.

Walsby E., et al., "Effects of the Aurora Kinase Inhibitors AZD1152-HQPA and ZM447439 on Growth Arrest and Polyploidy in Acute Myeloid Leukemia Cell Lines and Primary Blasts," Haematologica, 2008, vol. 93 (5), pp. 662-669.

Xu H.T., et al., "Expression of Serine Threonine Kinase 15 is Associated With Poor Differentiation in Lung Squamous Cell Carcinoma and Adenocarcinoma," Pathology International, 2006, vol. 56 (7), pp. 375-380.

Yang S.B., et al., "Amplification and Overexpression of Aurora-A in Esophageal Squamous Cell Carcinoma," Oncology Reports, 2007, vol. 17 (5), pp. 1083-1088.

Zeng W.F., et al., "Aurora B Expression Correlates With Aggressive Behaviour in Glioblastoma Multiforme," Journal of Clinical Pathology, 2007, vol. 60 (2), pp. 218-221.

Zhoa X., et al., "Mutation of p53 and Overexpression of STK15 in Laryngeal Squamous-Cell Carcinoma," Chinese Journal of Oncology, 2005, vol. 27 (3), pp. 134-137.

INDAZOLE INHIBITORS OF KINASE

CROSS-REFERENCE TO RELATED APPLICATIONS

This application claims priority to U.S. Provisional Application Ser. No. 61/333,843 filed May 12, 2010, which is incorporated by reference in its entirety.

FIELD OF THE INVENTION

This invention pertains to compounds that inhibit protein kinases such as Aurora-kinases and the VEGFR and PDGFR families of kinases, compositions containing the compounds, and methods of treating diseases using the compounds.

BACKGROUND OF THE INVENTION

Mitosis is a process by which a complete copy of a duplicated genome is segregated by the microtuble spindle apparatus into two daughter cells. Aurora-kinases, key mitotic regulators required for genome stability, have been found to be overexpressed in human tumors. There is therefore an existing need in the therapeutic arts for compounds which inhibit Aurora-kinases, compositions comprising the inhibitors and methods of treating diseases during which Aurora-kinases are unregulated or overexpressed.

The reversible phosphorylation of proteins is one of the primary biochemical mechanisms mediating eukaryotic cell signaling. This reaction is catalyzed by protein kinases that transfer the g-phosphate group of ATP to hydroxyl groups on target proteins. 518 such enzymes exist in the human genome of which ~90 selectively catalyze the phosphorylation of tyrosine hydroxyl groups Cytosolic tyrosine kinases reside intracellularly whereas receptor tyrosine kinases (RTKs) possess both extracellular and intracellular domains and function as membrane spanning cell surface receptors. As such, RTKs mediate the cellular responses to environmental signals and facilitate a broad range of cellular processes including proliferation, migration and survival.

RTK signaling pathways are normally highly regulated, yet their over-activation has been shown to promote the growth, survival and metastasis of cancer cells. Dysregulated RTK signaling occurs through gene over-expression or mutation and has been correlated with the progression of various human cancers.

The VEGF receptor (VEGFR) family consists of three RTKs, KDR (kinase insert domain-containing receptor; VEGFR2), FLT1 (Fms-like tyrosine kinase; VEGFR1), and FLT4 (VEGFR3). These receptors mediate the biological function of the vascular endothelial growth factors (VEGF-A, -B, -C, -D, -E and placenta growth factor (P1GF)), a family of homodimeric glycoproteins that bind the VEGF receptors with varying affinities.

KDR is the major mediator of the mitogenic, angiogenic and permeability-enhancing effects of VEGF-A, hereafter referred to as VEGF. Many different cell types are able to produce VEGF, yet its biological activity is limited predominately to the vasculature by way of the endothelial cell-selective expression of KDR. Not surprisingly, the VEGF/KDR axis is a primary mediator of angiogenesis, the means by which new blood vessels are formed from preexisting vessels.

FLT1 binds VEGF, VEGF-B and placental growth factor. FLT1 is expressed on the surface of smooth muscle cells, monocytes and hematopoietic stems cells in addition to endothelial cells. Activation of FLT1 signaling results in the mobilization of marrow-derived endothelial progenitor cells that are recruited to tumors where they contribute to new blood vessel formation.

FLT4 mediates the signaling of VEGF-C and VEGF-D, which mediate formation of tumor-associated lymphatic vessels (lymphangiogenesis). Lymphatic vessels are one of the routes by which cancer cells disseminate from solid tumors during metastasis.

The PDGF receptor (PDGFR) family consists of five RTK's, PDGFR-a and -b, CSF1R, KIT, and FLT3.

The a and b isoforms of the platelet-derived growth factor (PDGF) receptors occur as homodimers or a/b heterodimers and are found most commonly on the surface of fibroblasts and smooth muscle cells. PDGFR-b contributes to tumor angiogenesis through the proliferation and migration of pericytes, the peri-endothelial cells that associate with and stabilize immature blood vessels. In gliomas, autocrine PDGFR stimulation, brought about by the co-expression of PDGF and PDGF receptors, mediates tumor cell proliferation and survival.

CSF-1R is encoded by the cellular homolog of the retroviral oncogene v-fms and is a major regulator of macrophage development. Macrophages are frequent components of tumor stroma and have been shown to modify the extracellular matrix in a manner beneficial to tumor growth and metastasis.

KIT is expressed by hematopoietic progenitor cells, mast cells, germ cells and by pacemaker cells in the gut (interstitial cells of Cajal). It contributes to tumor progression by two general mechanisms namely autocrine stimulation by its ligand, stem cell factor (SCF), and through mutations that result in ligand-independent kinase activity.

FLT3 is normally expressed on hematopoietic stem cells where its interaction with FLT3 ligand (FL) stimulates stem cell survival, proliferation and differentiation. In addition to being over-expressed in various leukemia cells, FLT3 is frequently mutated in hematological malignancies with approximately one-third of patients with acute myeloid leukemia (AML) harboring activating mutations.

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

The present invention has numerous embodiments. One embodiment of this invention, therefore, pertains to compounds that have formula (I)

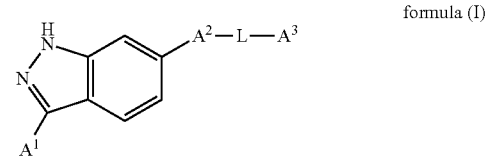

formula (I)

wherein $A^1$, $A^2$, L, and $A^3$ are as defined below and subsets therein.

Also provided are pharmaceutically acceptable compositions comprising a therapeutically effective amount of a compound of formula (I) a pharmaceutically acceptable salt in combination with a pharmaceutically suitable carrier.

One embodiment is directed A method of treating cancer in a mammal comprising administering thereto a therapeutically acceptable amount of a compound or pharmaceutically acceptable salt of formula (I). In yet another embodiment pertains to a method of decreasing tumor volume in a mammal comprising administering thereto a therapeutically acceptable amount of a compound or pharmaceutically acceptable salt of formula (I).

Still another embodiment pertains to methods of treating bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer in a mammal, the methods comprising administering thereto a therapeutically effective amount of a compound having formula (I), with or without also administering radiotherapy thereto.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 7 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 7 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—$NH_2$.

The term "oxy" (alone or in combination with another term(s)) means an ether substituent, and may be depicted as —O—.

The term "alkyloxy" (alone or in combination with another term(s)) means an alkylether substituent, i.e., —O-alkyl. Examples of such a substituent include methoxy (—O—$CH_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-$NH_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —$S(O)_2$—.

The term "aminosulfonyl" (alone or in combination with another term(s)) means —$S(O)_2$—$NH_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$— prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts.

By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "KDR" means kinase insert domain receptor (a type III receptor tyrosine kinase) and is also known as FLK1, VEGFR, VEGFR2, and CD309.

The term "VEGFR" means vascular endothelial growth factor receptor.

The term "PDGFR" means platelet-derived growth factor receptor.

Compounds

In one aspect, the present invention is directed, in part, to a class of compounds having a structure of formula (I):

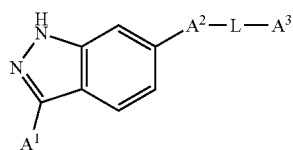

formula (I)

wherein $A^1$ is aryl or heteroaryl, which is optionally substituted with one or more $R^1$, $R^1$ is selected from the group consisting of $R^2$, alkyl, alkenyl, alkynyl, halogen, cyano, —$OR^3$, —$C(O)R^3$, —$C(O)OR^3$, —$C(O)NR^4R^5$, —$OC(O)R^3$, —$NR^4R^5$, —$NR^4C(O)R^5$, —$NHC(O)NHR^4$, —$NHS(O)_2R^3$, —$SR^3$, —$S(O)R^3$, —$SO_2R^3$, —$SO_2NR^4R^5$, —$N_3$, —$NO_2$, —$CF_3$, —$CF_2CF_3$, —$OCF_3$, and —$OCF_2CF_3$, wherein the $R^1$ alkyl, alkenyl, and alkynyl substituents are optionally substituted with one or more substituents selected from the group consisting of $R^6$, halogen, cyano, —$OR^3$, —$C(O)R^3$, —$C(O)OR^3$, —$C(O)NR^4R^5$, —$OC(O)R^3$, —$NR^4R^5$, and —$NR^4C(O)R^3$;

$R^2$ is aryl or heterocyclyl wherein the $R^2$ aryl and heterocyclyl substituents are optionally substituted with one or more substituents independently selected from the group consisting of $R^7$, halogen, cyano, —$OR^8$, —$C(O)R^8$, —$C(O)OR^8$, —$C(O)NR^9R^{10}$, —$OC(O)R^8$, —$NR^9R^{10}$, —$NR^9C(O)R^8$, —$NHC(O)NHR^9$, —$NHS(O)_2R^8$, —$SR^8$, —$S(O)R^8$, —$SO_2R^8$, —$SO_2NR^9R^{10}$, —$N_3$, —$NO_2$, —$CF_3$, —$CF_2CF_3$, —$OCF_3$, and —$OCF_2CF_3$;

$R^3$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^4$ and $R^5$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^6$ is aryl or heterocyclyl wherein the $R^6$ aryl and heterocyclyl substituents are optionally substituted with one or more substituents independently selected from the group consisting of $R^7$, halogen, cyano, —$OR^8$, —$C(O)R^8$, —$C(O)OR^8$, —$C(O)NR^9R^{10}$, —$OC(O)R^8$, —$NR^9R^{10}$, —$NR^9C(O)R^8$, —$NHC(O)NHR^9$, —$NHS(O)_2R^8$, —$SR^8$, —$S(O)R^8$, —$SO_2R^8$, —$SO_2NR^9R^{10}$, —$N_3$, —$NO_2$, —$CF_3$, —$CF_2CF_3$, —$OCF_3$, and —$OCF_2CF_3$;

$R^7$ is alkyl optionally substituted with one or more substituents selected from the group consisting of halogen, cyano, —$OR^{11}$, —$C(O)R^{11}$, —$C(O)OR^{11}$, —$C(O)NR^{12}R^{13}$, —$OC(O)R^{11}$, —$NR^{12}R^{13}$, —$NR^{12}C(O)R^{11}$, phenyl, and heterocycloalkyl;

$R^8$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^9$ and $R^{10}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^{11}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{12}$ and $R^{13}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$A^2$ is aryl or heteroaryl, which is optionally substituted with halogen;

L is $(CH_2)_mN(R^{14})C(O)N(R^{15})(CH_2)_n$, wherein m and n are independently 0 or 1; wherein $R^{14}$ and $R^{15}$ are independently selected from the group consisting of hydrogen and alkyl;

$A^3$ is aryl, cycloalkyl, cycloalkenyl, heterocyclyl, alkyl, alkenyl, or alkynyl, wherein (a) the $A^3$ alkyl, alkenyl, and alkynyl substituents are optionally substituted with one or more substituents selected from the group consisting of $R^{17}$, halogen, cyano, —$OR^{18}$, —$C(O)R^{18}$, —$C(O)OR^{18}$, —$C(O)NR^{19}R^{20}$, —$OC(O)R^{18}$, —$NR^{19}R^{20}$, —$NR^{19}C(O)R^{18}$, —$NHC(O)NHR^{19}$, —$NHS(O)_2R^{18}$, —$SR^{18}$, —$S(O)R^{18}$, —$SO_2R^{18}$, —$SO_2NR^{19}R^{20}$, —$N_3$, —$NO_2$, —$CF_3$, —$CF_2CF_3$, —$OCF_3$, and —$OCF_2CF_3$; (b) wherein the $A^3$ cycloalkyl, cycloalkenyl, aryl, and heterocyclyl substituents are optionally substituted with one or more $R^{16}$;

$R^{16}$ is selected from the group consisting of $R^{17}$, alkyl, alkenyl, alkynyl, halogen, cyano, —$OR^{21}$, —$C(O)R^{21}$, —$C(O)OR^{21}$, —$C(O)NR^{22}R^{23}$, —$OC(O)R^{21}$, —$NR^{22}R^{23}$, —$NR^{22}C(O)R^{21}$, —$NHC(O)NHR^{22}$, —$NHS(O)_2R^{21}$, —$SR^{21}$, —$S(O)R^{21}$, —$SO_2R^{21}$, —$SO_2NR^{22}R^{23}$, —$N_3$, —$NO_2$, —$CF_3$, —$CF_2CF_3$, —$OCF_3$; wherein the $R^{16}$ alkyl, alkenyl, and alkynyl substituents are optionally substituted with one or more substituents selected from the group consisting of aryl, heterocyclyl, cycloalkyl, halogen, cyano, —$OR^{21}$, —$C(O)R^{21}$, —$C(O)OR^{21}$, —$C(O)NR^{22}R^{23}$, —$NR^{22}R^{23}$, and —$NR^{22}C(O)R^{21}$;

$R^{17}$ is aryl or heterocyclyl wherein the $R^{17}$ aryl and heterocyclyl substituents are optionally substituted with one or more substituents independently selected from the group consisting of alkyl, alkenyl, alkynyl, halogen, cyano, $OR^{24}$, —$C(O)R^{24}$, —$C(O)OR^{24}$, —$C(O)NR^{25}R^{26}$, —$OC(O)R^{24}$, $NR^{25}R^{26}$, —$NR^{25}C(O)R^{26}$, —$NHC(O)NHR^{25}$, —$NHS(O)_2R^{24}$, —$SR^{24}$, —$S(O)R^{24}$, —$SO_2R^{24}$, —$SO_2NR^{25}R^{26}$, —$N_3$, —$NO_2$, —$CF_3$, —$CF_2CF_3$, —$OCF_3$;

$R^{18}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{19}$ and $R^{20}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^{21}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{22}$ and $R^{23}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^{24}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{25}$ and $R^{26}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

or a pharmaceutically acceptable salt thereof.

In one embodiment of formula (I), $A^1$ is phenyl, pyridyl, pyrimidinyl, pyridazinyl, pyrazyl, pyrrolyl, imidazyl, pyrazolyl, triazolyl, furanyl, thiophenyl, oxazolyl, isoxazolyl, thiazolyl, isothiazolyl, oxadiazolyl, and isothiazolyl. In other embodiments, $A^1$ is indolyl, isoindolyl, indazolyl, isoindazoyl, quinolinyl, benzoxazolyl, benzofuranyl, benzothiophenyl, benzothiazolyl, benzimidazolyl, benzotriazolyl, and 1,2,3,4-tetrahydroquinolinyl.

In one embodiment of formula (I), $A^1$ is selected from the group consisting of

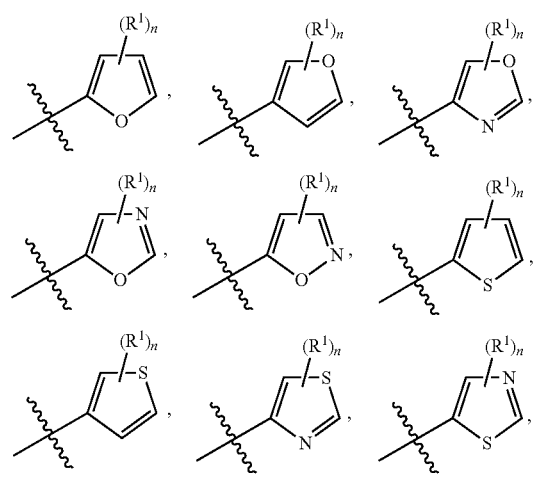

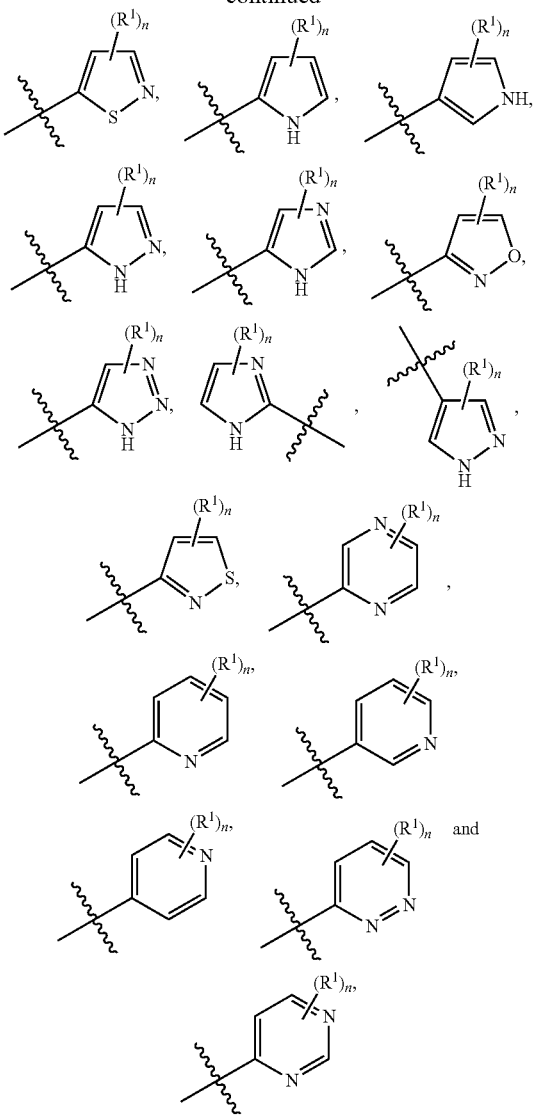

wherein n is 0, 1, or 2, and $R^1$ is as described in formula (I).

In one embodiment of formula (I), $A^1$ is optionally substituted with $R^1$, wherein $R^1$ is $R^2$, alkyl, halogen, cyano, —$OR^3$, —$C(O)R^3$, —$C(O)OR^3$, —$C(O)NR^4R^5$, —$OC(O)R^3$, —$NR^4R^5$, —$NR^4C(O)R^5$, $CF_3$, $CF_2CF_3$, $OCF_3$, and $OCF_2CF_3$; wherein $R^2$ is phenyl; wherein $R^3$, at each occurrence, is independently selected from the group consisting of hydrogen and alkyl; and wherein $R^4$ and $R^5$, at each occurrence, are independently selected from the group consisting of hydrogen and alkyl.

In one embodiment, $A^1$ is unsubstituted.

In one embodiment of formula (I), $A^1$ is selected from the group consisting of

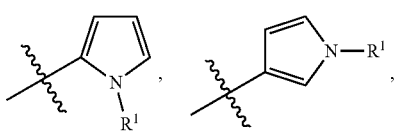

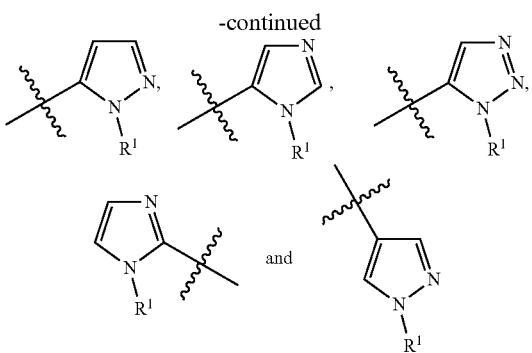

and $R^1$ is as described in formula (I). In one embodiment of formula (I), $A^1$ is substituted with $R^1$ on the nitrogen of the heterocyclic ring, wherein $R^1$ is an alkyl optionally substituted with 1 or 2 substituents selected from the group consisting of halogen, cyano, $OR^3$, $C(O)R^3$, $C(O)OR^3$, $NR^4R^5$, $C(O)NR^4R^5$, $NR^4C(O)R^3$, and $R^6$; wherein $R^3$, at each occurrence, is independently selected from the group consisting of hydrogen and alkyl; wherein $R^4$ and $R^5$, at each occurrence, are independently selected from the group consisting of hydrogen and alkyl; wherein $R^6$ is aryl or heterocyclyl wherein the $R^6$ aryl and heterocyclyl substituents are optionally substituted with one or more substituents independently selected from the group consisting of $R^7$, halogen, cyano, $-OR^8$, $-C(O)R^8$, $-C(O)OR^8$, $-NR^9R^{10}$, $-NR^9C(O)R^8$, $-C(O)NR^9R^{10}$; wherein $R^7$ is alkyl optionally substituted with one or more substituents selected from the group consisting of halogen, cyano, $-OR^{11}$, $-C(O)R^{11}$, $-C(O)OR^{11}$, $-C(O)NR^{12}R^{13}$, $-NR^{12}R^{13}$, and $-NR^{12}C(O)R^{11}$; wherein $R^8$, at each occurrence, is independently selected from the group consisting of hydrogen and alkyl; wherein $R^9$ and $R^{10}$, at each occurrence, are independently selected from the group consisting of hydrogen and alkyl; wherein $R^{11}$, at each occurrence, is independently selected from the group consisting of hydrogen and alkyl; and wherein $R^{12}$ and $R^{13}$, at each occurrence, are independently selected from the group consisting of hydrogen and alkyl;

In another embodiment, $A^1$ is substituted with $R^1$ on the nitrogen of the heterocyclic ring, wherein $R^1$ is selected from the group consisting of methyl, ethyl, n-propyl, iso-propyl, n-butyl, sec-butyl, or n-pentyl.

In yet another embodiment, $A^1$ is substituted with $R^1$ on the nitrogen of the heterocyclic ring, wherein $R^1$ is $R^1$ is $CH_2R^{27}$, $CH_2CH_2R^{27}$, $CH_2CH_2(CH_3)R^{27}$, or $CH_2CH_2CH_2R^{27}$; and wherein $R^{27}$ is selected from the group consisting of halogen, cyano, hydroxyl, $-OC_{1-4}$-alkyl, $-C(O)OH$, $-C(O)OC_{1-4}$-alkyl, $-C(O)NH_2$, $-C(O)NHC_{1-4}$-alkyl, and $-C(O)N(C_{1-4}$-alkyl$)_2$, and wherein $C_{1-4}$-alkyl is an unsubstituted branched or straight chain alkyl group. Alternatively, in another embodiment, $R^1$ is $CH_2R^{28}$, $CH_2CH_2R^{28}$, $CH_2CH_2(CH_3)R^{28}$, or $CH_2CH_2CH_2R^{28}$;

$R^{28}$ is selected from the group consisting of piperidinyl, piperazinyl, morpholino, tetrahydrofuranyl, pyrrolidinyl, 3-oxo-1-piperazinyl, 2-oxo-1-pyrrolidinyl, imidazolyl, pyridinyl, and 2-oxo-1-imidazolidinyl, wherein $R^{24}$ is optionally substituted with $-C_{1-4}$-alkyl, halogen, cyano, hydroxyl, $-OC_{1-4}$-alkyl, $-C(O)OH$, $-C(O)OC_{1-4}$-alkyl, $-C(O)C_{1-4}$-alkyl, $-C(O)NH_2$, $-C(O)NHC_{1-4}$-alkyl, and $-C(O)N(C_{1-4}$-alkyl$)_2$, and wherein $C_{1-4}$-alkyl is an unsubstituted branched or straight chain alkyl group.

In another embodiment, A $R^1$ is $R^2$, and wherein $R^2$ is phenyl or heterocycloalkyl. In a preferred embodiment, $R^2$ is piperidinyl, piperazinyl, morpholino, tetrahydrofuranyl, pyrrolidinyl, 3-oxo-1-piperazinyl, 2-oxo-1-pyrrolidinyl, imidazolyl, pyridinyl, and 2-oxo-1-imidazolidinyl, wherein $R^2$ is optionally substituted with $-C_{1-4}$-alkyl, halogen, cyano, hydroxyl, $-OC_{1-4}$-alkyl, $-C(O)OH$, $-C(O)OC_{1-4}$-alkyl, $-C(O)C_{1-4}$-alkyl, $-C(O)NH_2$, $-C(O)NHC_{1-4}$-alkyl, and $-C(O)N(C_{1-4}$-alkyl$)_2$, and wherein $C_{1-4}$-alkyl is an unsubstituted branched or straight chain alkyl group.

In yet another embodiment of formula (I), $A^2$ is phenyl.

In yet another embodiment of formula (I), L is $-NHC(O)NH-$.

In another embodiment of formula (I), $A^3$ is selected from the group consisting of phenyl, naphthalenyl, tetrahydronaphthalenyl, cyclopentyl, cyclopentenyl, cyclohexyl, cyclohexenyl, furanyl, pyridyl, and thiophenyl. In a preferred embodiment, $A^3$ is phenyl which is optionally substituted with 1, 2, or 3 $R^{16}$, wherein $R^{16}$ is selected from the group consisting of $-CH_3$, $-CH_2CH_3$, fluoro, chloro, bromo, cyano, $-NO_2$, $-OCH_3$, $-OCH_2CH_3$, $-CF_3$, $-CF_2CF_3$, $-OCF_3$, $-OCF_2CF_3$, $-NH_2$, $-N(CH_3)_2$, $-OH$, $-OPh$, $-C(=O)CH_3$, $-C(=O)CH_2CH_3$, and $C(=O)OH$.

In another aspect, the present invention is directed, in part, to a class of compounds having a structure of formula (II):

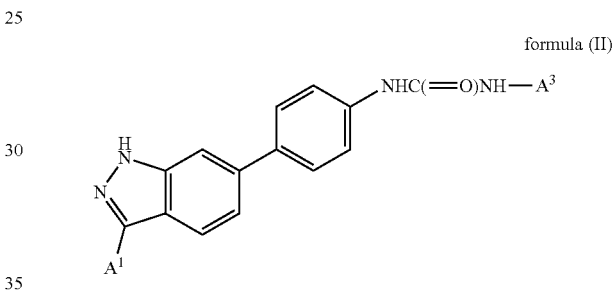

formula (II)

wherein $A^1$ and $A^3$ are as defined above.

In a preferred embodiment of formula (II), $A^1$ is selected from the group consisting of\

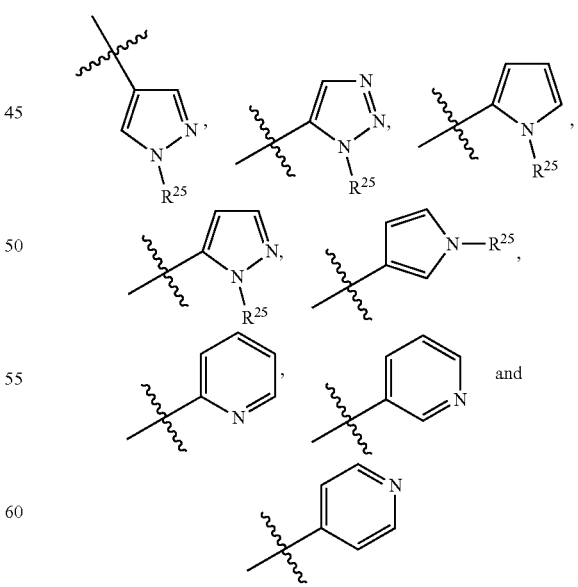

wherein $R^{25}$ is hydrogen or alkyl, wherein the alkyl is optionally substituted with hydroxyl, $-OC_{1-4}$-alkyl, $-C(O)OH$, or $-C(O)OC_{1-4}$-alkyl.

In another preferred embodiment of formula (II), $A^3$ is phenyl, wherein the phenyl is optionally substituted with —$CH_3$, —$CH_2CH_3$, fluoro, chloro, —$OCH_3$, —$OCH_2CH_3$, —$CF_3$, —$CF_2CF_3$, —$OCF_3$, and —$OCF_2CF_3$.

In another aspect, the present invention is directed, in part, to a class of compounds having a structure of formula (I):

In one embodiment of formula (I), $A^2$ is $R^2$, wherein $R^2$ is $CH_2R^{11}$, $CH_2CH_2R^{11}$, or $CH_2CH_2(CH_2)R^{11}$, and wherein $R^{11}$ is selected from the group consisting of CN, $NO_2$, $C_{1-4}$-haloalkyl, OH, $OC_{1-4}$-alkyl, $OC_{1-4}$-haloalkyl, C(O)OH, C(O)$OC_{1-4}$-alkyl, C(O)$NH_2$, C(O)NH$C_{1-4}$-alkyl, and C(O)N($C_{1-4}$-alkyl)$_2$, and wherein $C_{1-4}$-alkyl is an unsubstituted branched or straight chain alkyl group. In one embodiment, $R^{11}$ is OH or $CF_3$.

In another aspect, the present invention is directed, in part, to a class of compounds having a structure of formula (I): A compound having formula (I),

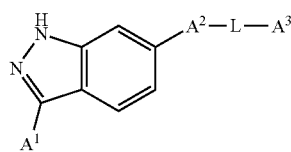

formula (I)

wherein $A^1$ is aryl or heteroaryl, which is optionally substituted with one or more $R^1$, $R^1$ is selected from the group consisting of $R^2$, alkyl, alkenyl, alkynyl, halogen, cyano, —$OR^3$, —C(O)$R^3$, —C(O)$OR^3$, —C(O)$NR^4R^5$, —OC(O)$R^3$, —$NR^4R^5$, —$NR^4$C(O)$R^5$, —NHC(O)NH$R^4$, —NHS(O)$_2R^3$, —$SR^3$, —S(O)$R^3$, —$SO_2R^3$, —$SO_2NR^4R^5$, —$N_3$, —$NO_2$, —$CF_3$, —$CF_2CF_3$, —$OCF_3$, and —$OCF_2CF_3$, wherein the $R^1$ alkyl, alkenyl, and alkynyl substituents are optionally substituted with one or more substituents selected from the group consisting of $R^6$, halogen, cyano, —$OR^3$, —C(O)$R^3$, —C(O)$OR^3$, —C(O)$NR^4R^5$, —OC(O)$R^3$, —$NR^4R^5$, and —$NR^4$C(O)$R^3$;

$R^2$ is aryl or heterocyclyl wherein the $R^2$ aryl and heterocyclyl substituents are optionally substituted with one or more substituents independently selected from the group consisting of $R^7$, halogen, cyano, —$OR^8$, —C(O)$R^8$, —C(O)$OR^8$, —C(O)$NR^9R^{10}$, —OC(O)$R^8$, —$NR^9R^{10}$, —$NR^9$C(O)$R^8$, —NHC(O)NH$R^9$, —NHS(O)$_2R^8$, —$SR^8$, —S(O)$R^8$, —$SO_2R^8$, —$SO_2NR^9R^{10}$, —$N_3$, —$NO_2$, —$CF_3$, —$CF_2CF_3$, —$OCF_3$, and —$OCF_2CF_3$;

$R^3$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^4$ and $R^5$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^6$ is aryl or heterocyclyl wherein the $R^6$ aryl and heterocyclyl substituents are optionally substituted with one or more substituents independently selected from the group consisting of $R^2$, halogen, cyano, —$OR^8$, —C(O)$R^8$, —C(O)$OR^8$, —OC(O)$R^8$, —$NR^9R^{10}$, —$NR^9$C(O)$R^8$, —NHC(O)NH$R^9$, —C(O)$NR^9R^{10}$, —$SR^8$, —S(O)$R^8$, —$SO_2R^8$, —OC(O)$OR^8$, —$SO_2NR^9R^{16}$, —$N_3$, —$NO_2$, —$CF_3$, —$CF_2CF_3$, —$OCF_3$, and —$OCF_2CF_3$;

$R^7$ is alkyl optionally substituted with one or more substituents selected from the group consisting of halogen, cyano, —$OR^{11}$, —C(O)$R^{11}$, —C(O)$OR^{11}$, —C(O)$NR^{12}R^{13}$, —OC(O)$R^{11}$, —$NR^{12}R^{13}$, —$NR^{12}$C(O)$R^{11}$, phenyl, and heterocyloalkyl;

$R^8$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^9$ and $R^{10}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^{11}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{12}$ and $R^{13}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$A^2$ is 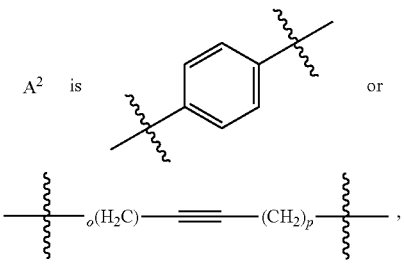 or wherein o and p are each independently 0, 1, or 2;

L is —(CH$_2$)$_m$N(R$^{14}$)C(O)—, —C(O)N(R$^{15}$)(CH$_2$)$_n$—, —(CH$_2$)$_m$N(R$^{14}$)C(O)N(R$^{15}$)(CH$_2$)$_n$—, —(CH$_2$)$_m$N(R$^{14}$)S(O)$_2$—, or —S(O)$_2$N(R$^{15}$)(CH$_2$)$_n$—, wherein m and n are independently 0 or 1; wherein R$^{14}$ and R$^{15}$ are independently selected from the group consisting of hydrogen and alkyl;

$A^3$ is aryl, cycloalkyl, cycloalkenyl, heterocyclyl, alkyl, alkenyl, or alkynyl, wherein (a) the $A^3$ alkyl, alkenyl, and alkynyl substituents are optionally substituted with one or more substituents selected from the group consisting of $R^{17}$, halogen, cyano, —$OR^{18}$, —C(O)$R^{18}$, —C(O)$OR^{18}$, —OC(O)$R^{18}$, —$NR^{19}R^{20}$, —$NR^{19}$C(O)$R^{18}$, —NHC(O)NH$R^{20}$, —C(O)$NR^{19}R^{20}$, SR$^{18}$, —S(O)$R^{18}$, —$SO_2R^{18}$, —OC(O)$OR^{18}$, —$SO_2NR^{19}R^{20}$, —$N_3$, —$NO_2$, —$CF_3$, —$CF_2CF_3$, —$OCF_3$, and —$OCF_2CF_3$; (b) wherein the $A^3$ cycloalkyl, cycloalkenyl, aryl, and heterocyclyl substituents are optionally substituted with one or more $R^{16}$;

$R^{16}$ is selected from the group consisting of $R^{17}$, alkyl, alkenyl, alkynyl, halogen, cyano, —$OR^{21}$, —C(O)$R^{21}$, —C(O)OR²¹, —OC(O)R²¹, —NR²²R²³, —NR²²C(O)R²¹, —NHC(O)NHR²², —C(O)NR²²R²³, —SR²¹, —S(O)R²¹, —SO₂R²¹, —OC(O)OR²¹, —SO₂NR²²R²³, —N₃, —NO₂, —CF₃, —CF₂CF₃, —OCF₃; wherein the R¹⁶ alkyl, alkenyl, and alkynyl substituents are optionally substituted with one or more substituents selected from the group consisting of aryl, heterocyclyl, cycloalkyl, halogen, cyano, —OR²¹, —C(O)R²¹, —C(O)OR²¹, —C(O)NR²²R²³, —OC(O)R²¹, —NR²²R²³, and —NR²²C(O)R²¹;

R¹⁷ is aryl or heterocyclyl wherein the R¹⁷ aryl and heterocyclyl substituents are optionally substituted with one or more substituents independently selected from the group consisting of alkyl, alkenyl, alkynyl, halogen, cyano, —OR²¹, —C(O)R²¹, —C(O)OR²¹, —OC(O)R²¹, —NR²²R²³, —NR²²C(O)R²¹, —NHC(O)NHR²², —C(O)NR²²R²³, —SR²¹, —S(O)R²¹, —SO₂R²¹, —OC(O)OR²¹, —SO₂NR²²R²³, —N₃, —NO₂, —CF₃, —CF₂CF₃, —OCF₃;

R¹⁸, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

R¹⁹ and R²⁰, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

R²¹, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

R²² and R²³, at each occurrence, are independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

or a pharmaceutically acceptable salt thereof.

In one embodiment of formula (I), A¹ is selected from the group consisting of

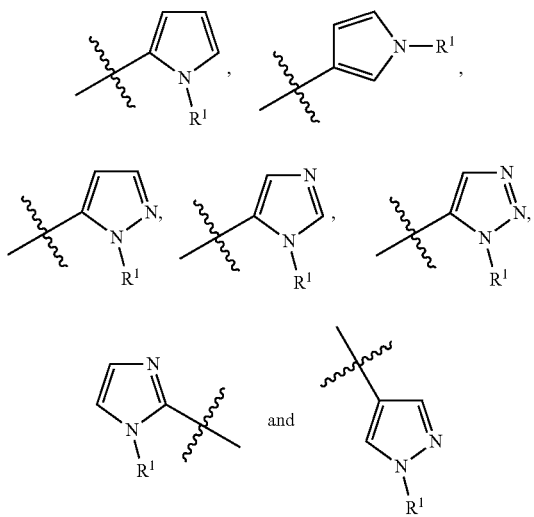

and R¹ is as described in formula (I). In one embodiment of formula (I), A¹ is substituted with R¹ on the nitrogen of the heterocyclic ring, wherein R¹ is an alkyl optionally substituted with 1 or 2 substituents selected from the group consisting of halogen, cyano, OR³, C(O)R³, C(O)OR³, NR⁴R⁵, C(O)NR⁴R⁵, NR⁴C(O)R³, and R⁶; wherein R³, at each occurrence, is independently selected from the group consisting of hydrogen and alkyl; wherein R⁴ and R⁵, at each occurrence, are independently selected from the group consisting of hydrogen and alkyl; wherein R⁶ is aryl or heterocyclyl wherein the R⁶ aryl and heterocyclyl substituents are optionally substituted with one or more substituents independently selected from the group consisting of R⁷, halogen, cyano, —OR⁸, —C(O)R⁸, —C(O)OR⁸, —NR⁹R¹⁰, —NR⁹C(O)R⁸, —C(O)NR⁹R¹⁰; wherein R⁷ is alkyl optionally substituted with one or more substituents selected from the group consisting of halogen, cyano, —OR¹¹, —C(O)R¹¹, —C(O)OR¹¹, —C(O)NR¹²R¹³, —NR¹²R¹³, and —NR¹²C(O)R¹¹; wherein R⁸, at each occurrence, is independently selected from the group consisting of hydrogen and alkyl; wherein R⁹ and R¹⁰, at each occurrence, are independently selected from the group consisting of hydrogen and alkyl; wherein R¹¹, at each occurrence, is independently selected from the group consisting of hydrogen and alkyl; and wherein R¹² and R¹³, at each occurrence, are independently selected from the group consisting of hydrogen and alkyl;

In another embodiment, A¹ is substituted with R¹ on the nitrogen of the heterocyclic ring, wherein R¹ is selected from the group consisting of methyl, ethyl, n-propyl, iso-propyl, n-butyl, sec-butyl, or n-pentyl.

In yet another embodiment, A¹ is substituted with R¹ on the nitrogen of the heterocyclic ring, wherein R¹ is R¹ is CH₂R²⁷, CH₂CH₂R²⁷, CH₂CH₂(CH₃)R²⁷, or CH₂CH₂CH₂R²⁷; and wherein R²⁷ is selected from the group consisting of halogen, cyano, hydroxyl, —OC₁₋₄-alkyl, —C(O)OH, —C(O)OC₁₋₄-alkyl, —C(O)NH₂, —C(O)NHC₁₋₄-alkyl, and —C(O)N(C₁₋₄-alkyl)₂, and wherein C₁₋₄-alkyl is an unsubstituted branched or straight chain alkyl group. Alternatively, in another embodiment, R¹ is CH₂R²⁸, CH₂CH₂R²⁸, CH₂CH₂(CH₃)R²⁸, or CH₂CH₂CH₂R²⁸;

R²⁸ is selected from the group consisting of piperidinyl, piperazinyl, morpholino, tetrahydrofuranyl, pyrrolidinyl, 3-oxo-1-piperazinyl, 2-oxo-1-pyrrolidinyl, imidazolyl, pyridinyl, and 2-oxo-1-imidazolidinyl, wherein R²⁴ is optionally substituted with —C₁₋₄-alkyl, halogen, cyano, hydroxyl, —OC₁₋₄-alkyl, —C(O)OH, —C(O)OC₁₋₄-alkyl, —C(O)C₁₋₄-alkyl, —C(O)NH₂, —C(O)NHC₁₋₄-alkyl, and —C(O)N(C₁₋₄-alkyl)₂, and wherein C₁₋₄-alkyl is an unsubstituted branched or straight chain alkyl group.

In another embodiment, A R¹ is R², and wherein R² is phenyl or heterocycloalkyl. In a preferred embodiment, R² is piperidinyl, piperazinyl, morpholino, tetrahydrofuranyl, pyrrolidinyl, 3-oxo-1-piperazinyl, 2-oxo-1-pyrrolidinyl, imidazolyl, pyridinyl, and 2-oxo-1-imidazolidinyl, wherein R² is optionally substituted with —C₁₋₄-alkyl, halogen, cyano, hydroxyl, —OC₁₋₄-alkyl, —C(O)OH, —C(O)OC₁₋₄-alkyl, —C(O)C₁₋₄-alkyl, —C(O)NH₂, —C(O)NHC₁₋₄-alkyl, and —C(O)N(C₁₋₄-alkyl)₂, and wherein C₁₋₄-alkyl is an unsubstituted branched or straight chain alkyl group.

In another embodiment of formula (I), A³ is selected from the group consisting of phenyl, naphthalenyl, tetrahydronaphthalenyl, cyclopentyl, cyclopentenyl, cyclohexyl, cyclohexenyl, furanyl, pyridyl, and thiophenyl. In a preferred embodiment, A³ is phenyl which is optionally substituted with 1, 2, or 3 R¹⁶, wherein R¹⁶ is selected from the group consisting of —CH₃, —CH₂CH₃, fluoro, chloro, bromo, cyano, —NO₂, —OCH₃, —OCH₂CH₃, —CF₃, —CF₂CF₃, —OCF₃, —OCF₂CF₃, —NH₂, —N(CH₃)₂, —OH, —OPh, —C(=O)CH₃, —C(=O)CH₂CH₃, and C(=O)OH.

Specific embodiments contemplated as part of the invention include, but are not limited to, compounds of formula (I), for example:

N-(3-fluorophenyl)-N'-{4-[3-(1-methyl-1H-pyrazol-4-yl)-1H-indazol-6-yl]phenyl}urea;
N-(3-methylphenyl)-N'-{4-[3-(1-methyl-1H-pyrazol-4-yl)-1H-indazol-6-yl]phenyl}urea;
N-(3-methylphenyl)-N'-{4-[3-(1H-1,2,3-triazol-5-yl)-1H-indazol-6-yl]phenyl}urea;
N-(3-methylphenyl)-N'-{4-[3-(1H-pyrrol-2-yl)-1H-indazol-6-yl]phenyl}urea;
N-(3-methylphenyl)-N'-(4-{3-[1-(2-morpholin-4-ylethyl)-1H-pyrazol-4-yl]-1H-indazol-6-yl}phenyl)urea;
N-(3-fluorophenyl)-N'-(4-{3-[1-(2-morpholin-4-ylethyl)-1H-pyrazol-4-yl]-1H-indazol-6-yl}phenyl)urea;
N-(3-methylphenyl)-N'-[4-(3-thien-3-yl-1H-indazol-6-yl)phenyl]urea;
N-(3-fluorophenyl)-N'-{4-[3-(1H-pyrazol-5-yl)-1H-indazol-6-yl]phenyl}urea;
N-(3-fluorophenyl)-N'-{4-[3-(1H-pyrazol-4-yl)-1H-indazol-6-yl]phenyl}urea;
N-(3-fluorophenyl)-N'-(4-{3-[1-(2-hydroxyethyl)-1H-pyrazol-4-yl]-1H-indazol-6-yl}phenyl)urea;
N-(4-{3-[1-(2-hydroxyethyl)-1H-pyrazol-4-yl]-1H-indazol-6-yl}phenyl)-N'-[3-(trifluoromethyl)phenyl]urea;
N-(4-{3-[1-(2-hydroxyethyl)-1H-pyrazol-4-yl]-1H-indazol-6-yl}phenyl)-N'-(3-methylphenyl)urea;
N-(3-fluorophenyl)-N'-{4-[3-(1-propyl-1H-pyrazol-4-yl)-1H-indazol-6-yl]phenyl}urea;
N-(3-fluorophenyl)-N'-(4-{3-[1-(2-hydroxy-2-methylpropyl)-1H-pyrazol-4-yl]-1H-indazol-6-yl}phenyl)urea;
N-(3-fluorophenyl)-N'-{4-[3-(1-piperidin-4-yl-1H-pyrazol-4-yl)-1H-indazol-6-yl]phenyl}urea;
N-(3-methylphenyl)-N'-{3-[3-(1-methyl-1H-pyrazol-4-yl)-1H-indazol-6-yl]phenyl}urea;
N-{4-[3-(1-methyl-1H-pyrazol-4-yl)-1H-indazol-6-yl]phenyl}-N'-[3-(trifluoromethyl)phenyl]urea;
N-{4-[3-(1-methyl-1H-pyrazol-4-yl)-1H-indazol-6-yl]phenyl}-N'-[4-(trifluoromethyl)phenyl]urea;
N-(4-chlorophenyl)-N'-{4-[3-(1-methyl-1H-pyrazol-4-yl)-1H-indazol-6-yl]phenyl}urea;
N-(3-fluorophenyl)-N'-{4-[3-(1H-1,2,3-triazol-5-yl)-1H-indazol-6-yl]phenyl}urea;
N-(3-chlorophenyl)-N'-{4-[3-(1-methyl-1H-pyrazol-4-yl)-1H-indazol-6-yl]phenyl}urea;
N-(2-chlorophenyl)-N'-{4-[3-(1-methyl-1H-pyrazol-4-yl)-1H-indazol-6-yl]phenyl}urea;
N-(3-fluorophenyl)-N'-{4-[3-(1-methyl-1H-pyrazol-4-yl)-1H-indazol-6-yl]benzyl}urea;
N-{4-[3-(1-methyl-1H-pyrazol-4-yl)-1H-indazol-6-yl]phenyl}-N'-[3-(trifluoromethoxy)phenyl]urea;
N-{4-[3-(1-methyl-1H-pyrazol-4-yl)-1H-indazol-6-yl]phenyl}-N'-[2-(trifluoromethyl)phenyl]urea;
N-{4-[3-(1-methyl-1H-pyrazol-4-yl)-1H-indazol-6-yl]phenyl}-N'-[2-(trifluoromethoxy)phenyl]urea;
N-{4-[3-(1-methyl-1H-pyrazol-4-yl)-1H-indazol-6-yl]phenyl}-N'-[4-(trifluoromethoxy)phenyl]urea;
N-(3-fluorophenyl)-N'-{3-[3-(1-methyl-1H-pyrazol-4-yl)-1H-indazol-6-yl]benzyl}urea;
N-(5-methylisoxazol-3-yl)-N'-{4-[3-(1-methyl-1H-pyrazol-4-yl)-1H-indazol-6-yl]phenyl}urea;
3-fluoro-N-{4-[3-(1-methyl-1H-pyrazol-4-yl)-1H-indazol-6-yl]benzyl}benzamide;
N-(3-methylphenyl)-N'-[4-(3-phenyl-1H-indazol-6-yl)phenyl]urea;
N-(3-methylphenyl)-N'-[4-(3-pyridin-3-yl-1H-indazol-6-yl)phenyl]urea;
N-(3-methylphenyl)-N'-[3-(3-pyridin-3-yl-1H-indazol-6-yl)phenyl]urea;
N-(3-methylphenyl)-N'-{4-[3-(1,3-thiazol-4-yl)-1H-indazol-6-yl]phenyl}urea;
2-(4-{6-[4-({[(3-fluorophenyl)amino]carbonyl}amino)phenyl]-1H-indazol-3-yl}-1H-pyrazol-1-yl)-N-methylpropanamide;
N-{4-[3-(1H-indol-2-yl)-1H-indazol-6-yl]phenyl}-N'-(3-methylphenyl)urea;
N-methyl-2-[4-(6-[4-[(phenylsulfonyl)amino]phenyl]-1H-indazol-3-yl)-1H-pyrazol-1-yl]propanamide;
3-fluoro-N-{4-[3-(1-methyl-1H-pyrazol-4-yl)-1H-indazol-6-yl]phenyl}benzamide;
N-{4-[3-(1-methyl-1H-pyrazol-4-yl)-1H-indazol-6-yl]phenyl}-N'-[3-(pyrrolidin-1-ylmethyl)phenyl]urea;
N-(3-fluorophenyl)-N'-(4-{3-[1-(2-pyrrolidin-1-ylethyl)-1H-pyrazol-4-yl]-1H-indazol-6-yl}phenyl)urea;
N-{4-[3-(1H-indol-3-yl)-1H-indazol-6-yl]phenyl}-N'-(3-methylphenyl)urea;
N-[4-(3-{1-[(2R)-2-hydroxypropyl]-1H-pyrazol-4-yl]-1H-indazol-6-yl)phenyl]-N'-(3-methylphenyl)urea;
3-fluoro-N-{3-[3-(1-methyl-1H-pyrazol-4-yl)-1H-indazol-6-yl]phenyl}benzamide; and
N-{3-chloro-4-[3-(1-methyl-1H-pyrazol-4-yl)-1H-indazol-6-yl]phenyl}-N'-(3-fluorophenyl)urea.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthioethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

Schemes

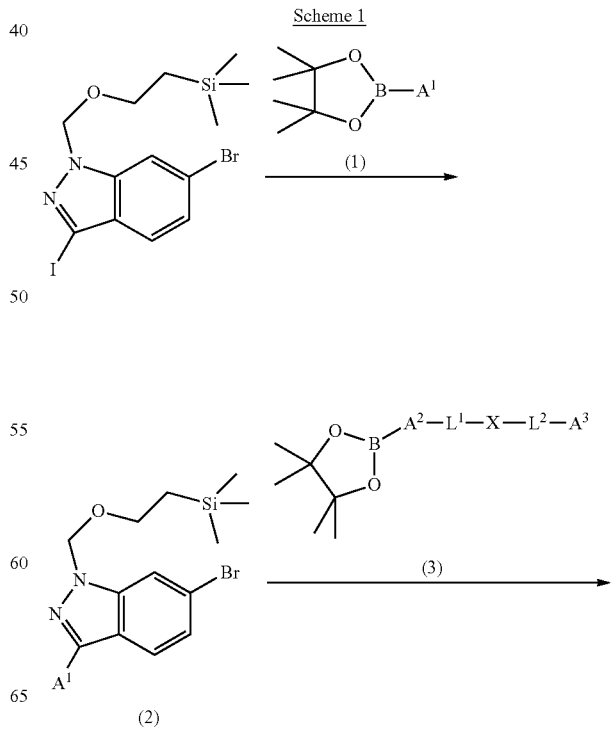

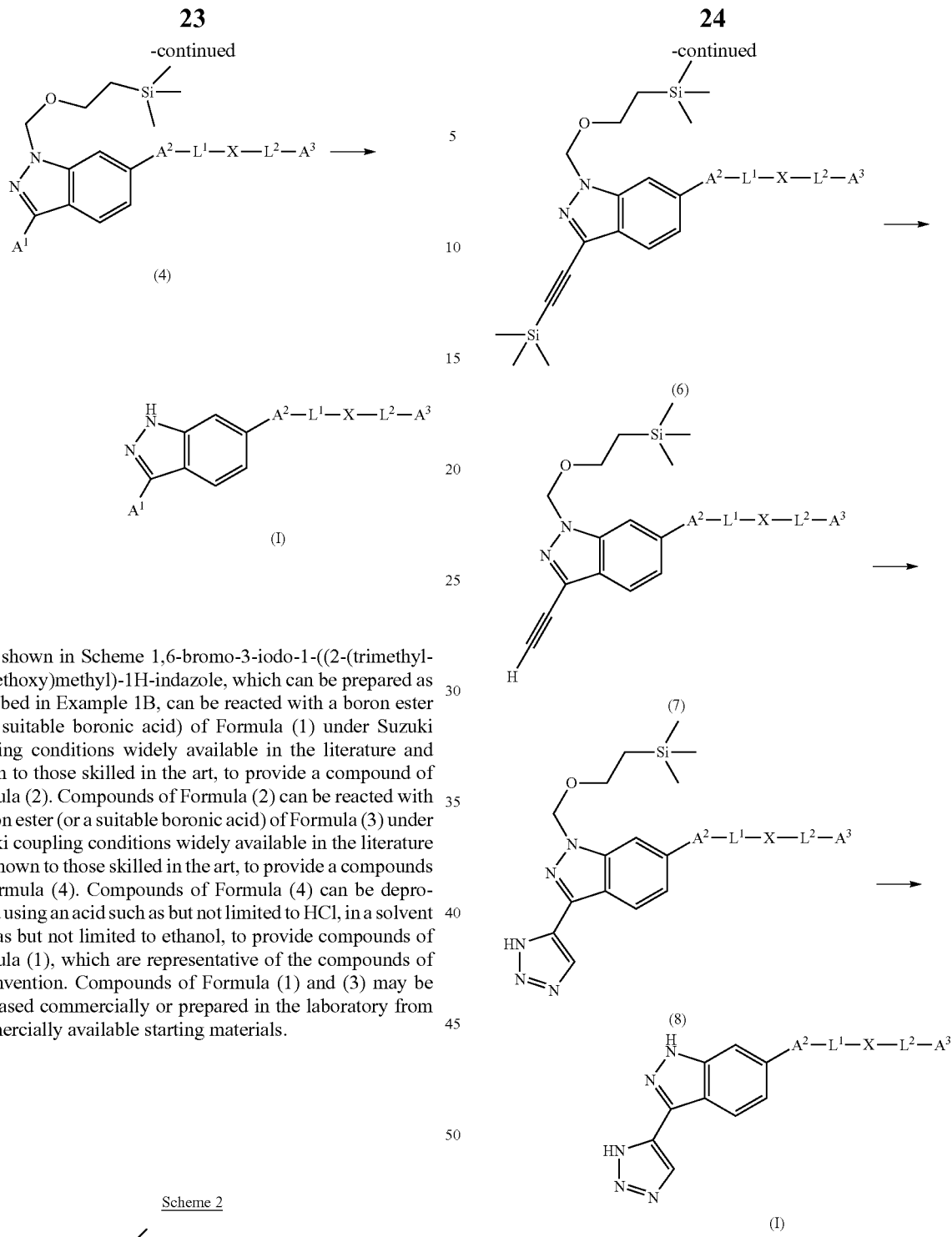

As shown in Scheme 1, 6-bromo-3-iodo-1-((2-(trimethylsilyl)ethoxy)methyl)-1H-indazole, which can be prepared as described in Example 1B, can be reacted with a boron ester (or a suitable boronic acid) of Formula (1) under Suzuki coupling conditions widely available in the literature and known to those skilled in the art, to provide a compound of Formula (2). Compounds of Formula (2) can be reacted with a boron ester (or a suitable boronic acid) of Formula (3) under Suzuki coupling conditions widely available in the literature and known to those skilled in the art, to provide a compounds of Formula (4). Compounds of Formula (4) can be deprotected using an acid such as but not limited to HCl, in a solvent such as but not limited to ethanol, to provide compounds of Formula (1), which are representative of the compounds of this invention. Compounds of Formula (1) and (3) may be purchased commercially or prepared in the laboratory from commercially available starting materials.

Scheme 2

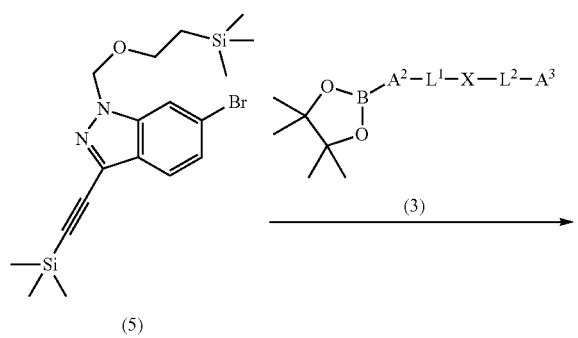

As shown in Scheme 2, compounds of Formula (5), which can be prepared as described in Example 21A, can be reacted with a boron ester (or a suitable boronic acid) of Formula (3) under Suzuki coupling conditions widely available in the literature and known to those skilled in the art, to provide a compound of Formula (6). Compounds of Formula (6) can be reacted with a base such as but not limited to potassium carbonate, in a solvent such as but not limited to methanol, to provide compounds of Formula (7). Compounds of Formula (7) can be reacted with trimethylsilyl azide and Cu(I)I catalyst to provide compounds of Formula (8). The reaction is typically performed at elevated temperatures in a solvent such as but not limited to N,N-dimethylformamide, methanol, or mixtures thereof. Compounds of Formula (1), which are representative of the compounds of this invention, can be prepared from compounds of Formula (8) as described in Scheme 1.

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all Aurora-kinase family members are expressed. In yet another aspect, compounds of this invention are expected to have utility in treatment of diseases or conditions during which protein kinases such as any or all KDR (VEGFR2) family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myeogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Involvement of Aurora Kinase in pancreatic carcinoma cells is reported in Zhu, J., et al., AURKA Amplification, Chromosome Instability, And Centrosome Abnormality in Human Pancreatic Carcinoma Cells. Cancer Genet. Cytogenet., 2005. 159(1): p. 10-17; and Li D., Zhu J., Firozi P. F., et al. Overexpression of Oncogenic STK15/BTAK/Aurora A Kinase in Human Pancreatic Cancer. Clin. Cancer Res. 2003; 9:991-7.

Involvement of Aurora Kinase in non-small cell lung carcinoma is reported in Smith, S. L., et al., Overexpression of Aurora B Kinase (AURKB) in Primary Non-Small Cell Lung Carcinoma is Frequent, Generally Driven from One Allele, and Correlates with the Level of Genetic Instability. Br. J. Cancer, 2005. 93(6): p. 719-729.

Involvement of Aurora Kinase in prostate cancer is reported in Chieffi, P., et al., Aurora B Expression Directly Correlates with Prostate Cancer Malignancy. Prostate, 2006. 66(3): p. 326-33; and Chieffi P., Cozzolino L., Kisslinger A., et al. Aurora B Expression Directly Correlates with Prostate Cancer Malignancy and Influences Prostate Cell Proliferation. Prostate 2006; 66:326-33.

Involvement of Aurora Kinase in head and neck squamous cell carcinoma is reported in Reiter, R., et al., Aurora Kinase A Messenger RNA Overexpression is Correlated with Tumor Progression and Shortened Survival in Head and Neck Squamous Cell Carcinoma. Clin Cancer Res, 2006. 12(17): p. 5136-41.

Involvement of Aurora Kinase in acute myeloid leukemia is reported in Walsby E., Walsh V., Pepper C., Burnett A., and Mills K. Haematologica. 2008 May; 93(5):662-9.

Involvement of Aurora Kinase in breast cancer is reported in Tanaka T., Kimura M., Matsunaga K., Fukada D., Mori H., Okano Y. Centrosomal Kinase AIK1 is Overexpressed in Invasive Ductal Carcinoma of The Breast. Cancer Res. 1999; 59:2041-4; Miyoshi Y., Iwao K., Egawa C., Noguchi S. Association of Centrosomal Kinase STK15/BTAK Mrna Expression with Chromosomal Instability in Human Breast Cancers. Int. J. Cancer 2001; 92:370-3; Hoque A., Carter J., Xia W., et al. Loss Of Aurora A/STK15/BTAK Overexpression Correlates with Transition of in Situ to Invasive Ductal Carcinoma of the Breast. Cancer Epidemiol. Biomarkers Prev. 2003; 12:1518-22; Royce M. E., Xia W., Sahin A. A., et al. STK15/Aurora-A Expression in Primary Breast Tumors is Correlated with Nuclear Grade But Not With Prognosis. Cancer 2004; 100:12-9; Bodvarsdottir S. K., Hilmarsdottir H., Birgisdottir V., Steinarsdottir M., Jonasson J. G., Eyfjord J. E., Aurora-A Amplification Associated with BRCA2 Mutation in Breast Tumours. Cancer Lett 2007; 248:96-102; Sen S., Zhou H., White R. A., A Putative Serine/Threonine Kinase Encoding Gene BTAK on Chromosome 20q13 is Amplified and Overexpressed in Human Breast Cancer Cell Lines. Oncogene 1997; 14:2195-200; Lo Y. L., Yu J. C., Chen S. T., et al. Breast Cancer Risk Associated with Genotypic Polymorphism of the Mitosisregulating Gene Aurora-A/STK15/BTAK. In. J. Cancer 2005; 115:276-83; Vidarsdottir L., Bodvarsdottir S. K., Hilmarsdottir H., Tryggvadottir L., Eyfjord J. E., Breast Cancer Risk Associated with AURKA 91T a Polymorphismin Relation to BRCA Mutations. Cancer Lett 2007; 250:206-12; Cox D. G., Hankinson S. E., Hunter D. J., Polymorphisms of the Aurka (STK15/Aurora Kinase) Gene and Breast Cancer Risk (United States). Cancer Causes Control 2006; 17:81-3; and Tchatchou S., Wirtenberger M., Hemminki K, et al. Aurora Kinases A and B and Familial Breast Cancer Risk. Cancer Lett 2007; 247:266-72.

Involvement of Aurora Kinase in lung cancer is reported in Smith S. L., Bowers N. L., Betticher D. C., et al. Overexpression Of Aurora B Kinase (AURKB) in Primary Non small Cell Lung Carcinoma is Frequent, Generally Driven Fromone Allele, and Correlates with the Level Of Genetic Instability. Br. J. Cancer 2005; 93:719-29; Xu H. T., Ma L., Qi F. J., et al. Expression of Serine Threonine Kinase15 is Associated with Poor Differentiation in Lung Squamous Cell Carcinoma and Adenocarcinoma. Pathol. Int. 2006; 56:375-80; Vischioni B., Oudejans J. J., Vos W., Rodriguez J. A., Giaccone G. Frequent Overexpression of Aurora B Kinase, a Novel Drug Target, in Non-Small Cell Lung Carcinoma Patients. Mol. Cancer. Ther. 2006; 5:2905-13; and Gu J., Gong Y., Huang M., Lu C., Spitz M. R., Wu X. Polymorphisms Of STK15 (Aurora-A) Gene and Lung Cancer Risk in Caucasians. Carcinogenesis 2007; 28:350-5.

Involvement of Aurora Kinase in bladder cancer is reported in Comperat E., Camparo P., Haus R., et al. Aurora-A/STK-15 is a Predictive Factor for Recurrent Behaviour in Non-Invasive Bladder Carcinoma: A Study Of 128 Cases of Non-Invasive Neoplasms. Virchows Arch 2007; 450:419-24; Fraizer G. C., Diaz M. F., Lee I. L., Grossman H. B., Sen S. Aurora-A/STK15/BTAK Enhances Chromosomal Instability in Bladder Cancer Cells. Int. J. Oncol. 2004; 25:1631-9; and Sen S., Zhou H., Zhang R. D., et al. Amplification/Overexpression of A Mitotic Kinase Gene in Human Bladder cancer. J. Natl. Cancer Inst. 2002; 94:1320-9.

Involvement of Aurora Kinase in esophageal cancer is reported in Tong T., Zhong Y., Kong J., et al. Overexpression of Aurora-A Contributes to Malignant Development of Human Esophageal Squamous Cell Carcinoma. Clin. Cancer Res. 2004; 10:7304-10; Yang S. B., Zhou X. B., Zhu H. X., et al. Amplification and Overexpression of Aurora-A in Esophageal Squamous Cell Carcinoma. Oncol. Rep. 2007; 17:1083-8; and Kimura M. T., Mori T., Conroy J., et al. Two Functional Coding Single Nucleotide Polymorphisms in STK15 (Aurora-A) Coordinately Increase Esophageal Cancer Risk. Cancer Res 2005; 65:3548-54.

Involvement of Aurora Kinase in brain cancer is reported in Araki K., Nozaki K., Ueba T., Tatsuka M., Hashimoto N. High Expression of Aurora-B/Aurora and Ipll-Like Midbody-Associated Protein (AIM-1) in Astrocytomas. J. Neurooncol. 2004; 67:53-64; Zeng W. F., Navaratne K., Prayson R. A., Weil R. J. Aurora B Expression Correlates with Aggressive Behaviour in Glioblastoma Multiforme. J. Clin. Pathol. 2007; 60:218-21; Reichardt W., Jung V., Brunner C., et al. The Putative Serine/Threonine Kinase Gene STK15 on Chromosome 20q13.2 is Amplified In Human Gliomas. Oncol. Rep. 2003; 10:1275-9; Klein A., Reichardt W., Jung V., Zang K. D., Meese E., Urbschat S. Overexpression and Amplification of STK15 Inhuman Gliomas. Int. J. Oncol. 2004; 25:1789-94; and Neben K., Korshunov A., Benner A., et al. Microarray Based Screening for Molecular Markers Nmedulloblastoma Revealed STK15 as Independent Predictor for Survival. Cancer Res 2004; 64:3103-11.

Involvement of Aurora Kinase in liver cancer is reported in Jeng Y. M., Peng S. Y., Lin C. Y., Hsu H. C. Overexpression and Amplification of Aurora-A in Hepatocellular Carcinoma. Clin. Cancer Res. 2004; 10:2065-71.

Involvement of Aurora Kinase in head and neck cancer is reported in Zhao X., Li F. C., Li Y. H., et al. [Mutation of p53 and Overexpression Of STK15 in Laryngeal Squamous-Cell Carcinoma]. Zhonghua Zhong Liu Za Zhi 2005; 27:134-7; Li F. C., Li Y. H., Zhao X., et al. [Deletion of p15 and p16 Genes and Overexpression of STK15 Gene in Human Laryngeal Squamous Cell Carcinoma]. Zhonghua Yi Xue Za Zhi 2003; 83:316-9; Reiter R., Gais P., Jutting U., et al. Aurora Kinase A Messenger RNA Overexpression is Correlated with Tumor Progression and Shortened Survival in Head and Neck Squamous Cell Carcinoma. Clin. Cancer Res. 2006; 12:5136-41; Qi G., Ogawa I., Kudo Y., et al. Aurora-B Expression and Its Correlation with Cell Proliferation and Metastasis in Oral Cancer. Virchows Arch 2007; 450:297-302; and Tatsuka M., Sato S., Kitajima S., et al. Overexpression of Aurora-A Potentiates HRAS-mediated Oncogenic Transformation and is Implicated in Oral Carcinogenesis. Oncogene 2005; 4:1122-7.

Involvement of Aurora Kinase in thyroid cancer is reported in Sorrentino R., Libertini S., Pallante P. L., et al. Aurora B Overexpression Associates with the Thyroid Carcinoma Undifferentiated Phenotype and is Required for Thyroid Carcinoma Cell Proliferation. J. Clin. Endocrinol. Metab. 2005; 90:928-35.

Involvement of Aurora Kinase in ovarian cancer is reported in Lassmann S., Shen Y., Jutting U., et al. Predictive Value of Aurora-A/STK15 Expression for Late Stage Epithelial Ovarian Cancer Patients Treated By Adjuvant Chemotherapy. Clin Cancer Res 2007; 13:4083-91; and Landen C. N., Jr., Lin Y. G., Immaneni A., et al. Overexpression of the Centrosomal Protein Aurora-A Kinase is Associated with Poor Prognosis in Epithelial Ovarian Cancer Patients. Clin. Cancer Res. 2007; 13:4098-104.

Involvement of Aurora Kinase in renal cancer is reported in Kurahashi T., Miyake H., Hara I., Fujisawa M. Significance of Aurora-A Expression in Renal Cell Carcinoma. Urol. Oncol. 2007; 25:128-33.

Involvement of Aurora Kinase in endometrium cancer is reported in Moreno-Bueno G., Sanchez-Estevez C., Cassia R., et al. Differential Gene Expression Profile in Endometrioid and Nonendometrioid Endometrial Carcinoma:STK15 is Frequently Overexpressed and Amplified in Nonendometrioid Carcinomas. Cancer Res. 2003; 63:5697-702.

Involvement of Aurora Kinase in gastric cancer is reported in Ju H., Cho H, Kim Y. S., et al. Functional Polymorphism 57Val>Ile of Aurora Kinase A Associated with Increased Risk of Gastric Cancer Progression. Cancer Lett. 2006; 242:273-9.

Involvement of Aurora Kinase in colon cancer is reported in Nishida N., Nagasaka T., Kashiwagi K., Boland C. R., Goel A. High Copy Amplification of the Aurora-A Gene is Associated with Chromosomal Instability Phenotype in Human Colorectal Cancers. Cancer Biol. Ther. 2007; 6:525-33; Bischoff J. R., Anderson L., Zhu Y., et al. A Homologue of Drosophila Aurora Kinase is Oncogenic and Amplified In Human Colorectal Cancers. EMBO J. 1998; 17:3052-65; Chen J., Sen S., Amos C. I., et al. Association Between Aurora-A Kinase Polymorphisms and Age of Onset of Hereditary Nonpolyposis Colorectal Cancer in a Caucasian Population. Mol. Carcinog. 2007; 46:249-56; Hienonen T., Salovaara R., Mecklin J. P., Jarvinen H., Karhu A., Aaltonen L. A. Preferential Amplification of AURKA 91A (11e31) in Familial Colorectal Cancers. Int. J. Cancer 2006; 118:505-8; and Ewart-Toland A., Briassouli P., de Koning J. P., et al. Identification of Stk6/STK15 as a Candidate Low-Penetrance Tumor-Susceptibility Gene in Mouse and Human. Nat. Genet. 2003; 34:403-12.

Involvement of Aurora Kinase in cancer is reported in Lin, Y. S., et al., Gene Expression Profiles of the Aurora Family Kinases. Gene Expr., 2006. 13(1): p. 15-26; and Ewart-Toland A., Dai Q., Gao Y. T., et al. Aurora-A/STK15 T+91A is a General Low Penetrance Cancer Susceptibility Gene: A Meta-Analysis of Multiple Cancer Types. Carcinogenesis 2005; 26:1368-73.

Involvement of KDR (VEGFR2) in cancer and studies using VEGF-targeted therapy is reported in Ellis, Lee M., Hicklin, Daniel J. VEGF-Targeted Therapy:Mechanisms Of Anti-Tumor Activity. Nature Reviews Cancer 2008; 8:579-591.

Involvement of Aurora-kinases in bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer is reported in Nature Reviews/ Cancer, Vol. 4 December, 2004.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCI, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-0,1-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-nl, combinations thereof and the like. Other agents include ALFAFERONE°, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (1) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTATAAE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECINT™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zoledronic acid), zorubicin and the like.

EXAMPLES

Example 1

N-(3-fluorophenyl)-N'-{4-[3-(1-methyl-1H-pyrazol-4-yl)-1H-indazol-6-yl]phenyl}urea Example 1A 6-bromo-3-iodo-1H-indazole A solution of 6-bromo-1H-indazole (10 g, 50.8 mmol, commercially available) in dioxane (200 ml) was treated with 3N aqueous NaOH (100 ml). The vigorously stirred mixture was treated with iodine (27.1 g, 107 mmol), added portionwise over 5 minutes then stirred for 60 minutes. The reaction was quenched with 200 ml of 20% citric acid solution, followed by 160 ml of saturated $NaHSO_3$ solution, then partitioned between ethyl acetate and water. The organic extract was dried with $MgSO_4$ and concentrated to a solid which was triturated with ether and pentane to afford the title compound.

Example 1B 6-bromo-3-iodo-1-((2-(trimethylsilyl)ethoxy)methyl)-1H-indazole

Example 1A (14.4 g, 44.6 mmol) was added to a 0° C. aqueous solution of potassium hydroxide (50.0 g, 892 mmol) in 200 ml water. The thick suspension was stirred for 10 minutes, and was diluted with $CH_2Cl_2$ (400 ml) and treated with tetrabutylammonium bromide (1.437 g, 4.46 mmol). (2-(chloromethoxy)ethyl)trimethylsilane (9.05 ml, 51.3 mmol) was then added dropwise over 50 minutes using a dropping funnel. The reaction was stirred for 1.5 hours at 0° C., and was extracted with $CH_2Cl_2$ (2×) and washed with water. The combined organics were dried with $MgSO_4$, concentrated and the residue was purified via silica gel flash chromatography eluting with $CH_2Cl_2$/hexane to afford the title compound.

Example 1C 6-bromo-3-(1-methyl-1H-pyrazol-4-yl)-1-((2-(trimethylsilyl)ethoxy)methyl)-1H-indazole A solution of Example 1B (0.500 g, 1.103 mmol) and 1-methyl-4-(4,4,5,5-tetramethyl-1,3,2-dioxaborolan-2-yl)-1H-pyrazole (0.275 g, 1.324 mmol) in toluene (8 ml) and ethanol (8 ml) under argon was treated with an aqueous solution of sodium carbonate (0.292 g, 2.76 mmol) in water (2 ml). Added $Pd(PPh_3)_4$ (0.217 g, 0.188 mmol) and the resulting heterogeneous mixture was refluxed at 80° C. for 2 hours, then stirred at room temperature for 18 hours. The reaction mixture was diluted with brine and extracted twice with ethyl acetate. The combined organics were dried with $MgSO_4$, concentrated and the residue purified via silica gel chromatography eluting with 0.5% methanol in $CH_2Cl_2$ to afford the title compound.

Example 1D 1-(3-fluorophenyl)-3-(4-(4,4,5,5-tetramethyl-1,3,2-dioxaborolan-2-yl)phenyl)urea A solution of 4-(4,4,5,5-tetramethyl-1,3,2-dioxaborolan-2-yl)aniline (1 g, 4.43 mmol) in $CH_2Cl_2$ (30 ml) under argon was treated with 1-fluoro-3-isocyanatobenzene (0.515 ml, 4.43 mmol), added dropwise. The reaction was stirred at room temperature for 18 hours, and was concentrated to a solid. Methylene chloride and hexane were added to precipitate the product, which was collected and dried in vacuo to afford the title compound.

Example 1E 1-(3-fluorophenyl)-3-(4-(3-(1-methyl-1H-pyrazol-4-yl)-1-((2-(trimethylsilyl)ethoxy)methyl)-1H-indazol-6-yl)phenyl)urea A mixture of Example 1C (187 mg, 0.459 mmol) and Example 1D (196 mg, 0.551 mmol) under argon was mixed with toluene (8.0 ml) and ethanol (8.0 ml). To this solution was added a solution of sodium carbonate (122 mg, 1.148 mmol) in water (2.0 ml), and then Pd(PPh$_3$)$_4$ (90 mg, 0.078 mmol). The reaction mixture was stirred at 80° C. for 2.5 hours under argon, allowed to cool to room temperature, diluted with brine, and extracted twice with ethyl acetate. The combined organics were dried with MgSO$_4$, filtered, and the residue was concentrated and purified by silica gel chromatography eluting with 1% methanol in CH$_2$Cl$_2$ to afford the title compound.

Example 1F

N-(3-fluorophenyl)-N'-{4-[3-(1-methyl-1H-pyrazol-4-yl)-1H-indazol-6-yl]phenyl}urea A suspension of Example 1E (45 mg, 0.081 mmol) in ethanol (6 ml) was treated with 2 ml of a 6N HCl solution, refluxed for 1 hour, then cooled and concentrated to near dryness. The residue was triturated with water and the resulting solid was collected, dissolved in methanol and CH$_2$Cl adsorbed onto Celite, and purified by silica gel chromatography (4% methanol in CH$_2$Cl$_2$) to afford the title compound. $^1$H NMR (300 MHz, DMSO-d$_6$) δ ppm 3.94 (s, 3 H) 6.79 (dt, J=8.82 Hz, 2.37 Hz, 1 H) 7.15 (d, J=8.14 Hz, 1 H) 7.32 (q, J=8.14 Hz, 1 H) 7.45 (dd, J=8.48 Hz, 1.36 Hz, 1 H) 7.51 (dt, J=2.37 Hz, 11.87 Hz, 1 H) 7.59 (m, 2 H) 7.69 (m, 3 H) 7.99 (s, 1 H) 8.05 (d, J=8.48 Hz, 1 H) 8.37 (s, 1 H) 8.89 (s, 1 H) 8.96 (s, 1 H) 12.94 (s, 1 H). MS (ESI(+)) m/e 427 (M+H)$^+$.

Example 2

N-(3-methylphenyl)-N'-{4-[3-(1-methyl-1H-pyrazol-4-yl)-1H-indazol-6-yl]phenyl}urea The title compound was prepared as described in Examples 1C-1F except substituting 1-isocyanato-3-methylbenzene for 1-fluoro-3-isocyanatobenzene. $^1$H NMR (300 MHz, DMSO-d$_6$) δ ppm 2.29 (s, 3 H) 3.94 (s, 3 H) 6.80 (d, J=7.14 Hz, 1 H) 7.17 (d, J=7.54 Hz, 1H) 7.23-7.28 (m, 1 H) 7.30-7.33 (m, 1 H) 7.45 (d, J=8.33 Hz, 1 H) 7.55-7.61 (m, 2 H) 7.66-7.72 (m, 3 H) 8.00 (s, 1 H) 8.04 (d, J=8.73 Hz, 1 H) 8.38 (s, 1 H) 8.62 (s, 1 H) 8.78 (s, 1 H) 12.94 (s, 1 H). MS (ESI(+)) m/e 423 (M+H)$^+$.

Example 3

N-(3-methylphenyl)-N'-{4-[3-(1H-1,2,3-triazol-5-yl)-1H-indazol-6-yl]phenyl}urea

The title compound was prepared as described in Example 21 except substituting 1-(4-(4,4,5,5-tetramethyl-1,3,2-dioxaborolan-2-yl)phenyl)-3-m-tolylurea for Example 1D. $^1$H NMR (300 MHz, DMSO-d$_6$) δ ppm 2.29 (s, 3 H) 6.80 (d, J=7.54 Hz, 1 H) 7.25 (d, J=8.33 Hz, 1 H) 7.32 (s, 1 H) 7.53 (d, J=8.33 Hz, 1 H) 7.56-7.62 (m, 2 H) 7.67-7.76 (m, 3 H) 8.22-8.33 (m, 2 H) 8.62 (s, 1 H) 8.79 (s, 1 H) 13.30 (s, 1 H) 15.11 (s, 1 H). MS (ESI(+)) m/e 410 (M+H)$^+$.

Example 4

N-(3-methylphenyl)-N'-{4-[3-(1H-pyrrol-2-yl)-1H-indazol-6-yl]phenyl}urea

The title compound was prepared as described in Example 1 except substituting 1-(tert-butoxycarbonyl)-1H-pyrrol-2-ylboronic acid and 1-isocyanato-3-methylbenzene for 1-methyl-4-(4,4,5,5-tetramethyl-1,3,2-dioxaborolan-2-yl)-1H-pyrazole and 1-fluoro-3-isocyanatobenzene, respectively in Examples 1C and 1D. $^1$H NMR (300 MHz, DMSO-d$_6$) δ ppm 2.29 (s, 3 H) 6.17-6.21 (m, 1 H) 6.73 (s, 1 H) 6.80 (d, J=7.54 Hz, 1 H) 6.85 (s, 1 H) 7.17 (t, J=7.54 Hz, 1 H) 7.25 (d, J=8.33 Hz, 1 H) 7.33 (s, 1 H) 7.45 (dd, J=8.73, 1.19 Hz, 1H) 7.55-7.62 (m, 2 H) 7.65-7.72 (m, 3 H) 8.05 (d, J=8.72 Hz, 1 H) 8.65 (s, 1 H) 8.81 (s, 1 H) 11.34 (s, 1 H) 12.94 (s, 1 H). MS (ESI(+)) m/e 408 (M+H)$^+$.

Example 5

N-(3-methylphenyl)-N'-(4-{3-[1-(2-morpholin-4-ylethyl)-1H-pyrazol-4-yl]-1H-indazol-6-yl}phenyl)urea The title compound was prepared as described in Example 1 except substituting 4-(2-(4-(4,4,5,5-tetramethyl-1,3,2-dioxaborolan-2-yl)-1H-pyrazol-1-yl)ethyl)morpholine and 1-isocyanato-3-methylbenzene for 1-methyl-4-(4,4,5,5-tetramethyl-1,3,2-dioxaborolan-2-yl)-1H-pyrazole and 1-fluoro-3-isocyanatobenzene, respectively in Examples 1C and 1D. $^1$H NMR (300 MHz, DMSO-d$_6$) δ ppm 2.29 (s, 3 H) 2.43-2.52 (m, 4 H) 2.79 (t, J=6.35 Hz, 2H) 3.57 (t, J=4.36 Hz, 4 H) 4.32 (t, J=6.35 Hz, 2 H) 6.80 (d, J=7.54 Hz, 1 H) 7.17 (t, J=7.54 Hz, 1 H) 7.25 (d, J=8.33 Hz, 1 H) 7.31 (s, 1 H) 7.45 (d, J=8.72 Hz, 1 H) 7.55-7.61 (m, 2 H) 7.66-7.72 (m, 3 H) 8.00 (s, 1 H) 8.04 (d, J=8.73 Hz, 1 H) 8.42 (s, 1 H) 8.61 (s, 1 H) 8.78 (s, 1 H) 12.94 (s, 1 H). MS (ESI(+)) m/e 522 (M+H)$^+$.

Example 6

N-(3-fluorophenyl)-N'-(4-{3-[1-(2-morpholin-4-ylethyl)-1H-pyrazol-4-yl]-1H-indazol-6-yl}phenyl)urea The title compound was prepared as described in Example 1 except substituting 4-(2-(4-(4,4,5,5-tetramethyl-1,3,2-dioxaborolan-2-yl)-1H-pyrazol-1-yl)ethyl)morpholine for 1-methyl-4-(4,4,5,5-tetramethyl-1,3,2-dioxaborolan-2-yl)-1H-pyrazole. $^1$H NMR (300 MHz, DMSO-d$_6$) δ ppm 2.42-2.53 (m, 4 H) 2.79 (t, J=6.74 Hz, 2 H) 3.57 (t, J=4.76 Hz, 4 H) 4.33 (t, J=6.35 Hz, 2 H) 6.79 (dt, J=8.72, 2.78 Hz, 1 H) 7.15 (d, J=8.33 Hz, 1 H) 7.32 (dd, J=7.93, 7.14 Hz, 1 H) 7.42-7.55 (m, 2 H) 7.56-7.62 (m, 2 H) 7.66-7.74 (m, 3 H) 8.01 (s, 1 H) 8.05 (d, J=8.33 Hz, 1 H) 8.42 (s, 1 H) 8.92 (s, 1 H) 8.99 (s, 1 H) 12.94 (s, 1 H). MS (ESI(+)) m/e 526 (M+H)$^+$.

Example 7

N-(3-methylphenyl)-N'-[4-(3-thien-3-yl-1H-indazol-6-yl)phenyl]urea

The title compound was prepared as described in Example 1 except substituting thiophen-3-ylboronic acid and 1-isocyanato-3-methylbenzene for 1-methyl-4-(4,4,5,5-tetramethyl-1,3,2-dioxaborolan-2-yl)-1H-pyrazole and 1-fluoro-3-isocyanatobenzene, respectively in Examples 1C and 1D. $^1$H NMR (300 MHz, DMSO-d$_6$) δ ppm 2.29 (s, 3 H) 6.80 (d, J=7.46 Hz, 1 H) 7.17 (t, J=7.46 Hz, 1 H) 7.26 (d, J=8.48 Hz, 1 H) 7.32 (s, 1 H) 7.50 (dd, J=8.48, 1.36 Hz, 1 H) 7.55-7.63 (m, 2 H) 7.67-7.76 (m, 5 H) 8.13-8.15 (m, 1 H) 8.17 (d, J=8.82 Hz, 1 H) 8.63 (s, 1 H) 8.80 (s, 1 H) 13.12 (s, 1 H). MS (ESI(+)) m/e 425 (M+H)$^+$.

Example 8

N-(3-fluorophenyl)-N'-{4-[3-(1H-pyrazol-5-yl)-1H-indazol-6-yl]phenyl}urea

The title compound was prepared by substituting 1H-pyrazol-5-ylboronic acid for 1-methyl-4-(4,4,5,5-tetramethyl-1,3,2-dioxaborolan-2-yl)-1H-pyrazole in Example 1C, then substituting the product for Example 1A in Example 1B, then following the procedures of Examples 1E and 1F. $^1$H NMR (300 MHz, DMSO-d$_6$) δ ppm 6.73-6.93 (m, 2 H) 7.16 (d, J=8.33 Hz, 1 H) 7.31 (dd, J=8.33, 7.14 Hz, 1 H) 7.44-7.56 (m, 2 H) 7.56-7.63 (m, 2 H) 7.66-7.75 (m, 4 H) 7.85 (s, 1 H) 8.31 (d, J=8.73 Hz, 1 H) 9.02 (s, 1 H) 9.09 (s, 1 H) 13.00 (s, 1 H) 13.03 (s, 1 H). MS (ESI(+)) m/e 413 (M+H)$^+$.

Example 9

N-(3-fluorophenyl)-N'-{4-[3-(1H-pyrazol-4-yl)-1H-indazol-6-yl]phenyl}urea

The title compound was prepared as described in Example 1 except substituting 4-(4,4,5,5-tetramethyl-1,3,2-dioxaborolan-2-yl)-1-((2-(trimethylsilyl)ethoxy)methyl)-1H-pyrazole for 1-methyl-4-(4,4,5,5-tetramethyl-1,3,2-dioxaborolan-2-yl)-1H-pyrazole in Example 1C. $^1$H NMR (300 MHz, DMSO-d$_6$) δ ppm 6.80 (dt, J=8.72, 2.78 Hz, 1 H) 7.15 (d, J=8.33 Hz, 1 H) 7.32 (dd, J=7.93, 7.14 Hz, 1 H) 7.44 (d, J=8.73 Hz, 1 H) 7.52 (d, J=12.29 Hz, 1 H) 7.56-7.63 (m, 2 H) 7.65-7.74 (m, 3 H) 8.04-8.12 (m, 2 H) 8.39 (s, 1 H) 8.91 (s, 1 H) 8.98 (s, 1 H) 12.93 (s, 1 H) 13.09 (s, 1 H). MS (ESI(+)) m/e 413 (M+H)$^+$.

Example 10

N-(3-fluorophenyl)-N'-(4-{3-[1-(2-hydroxyethyl)-1H-pyrazol-4-yl]-1H-indazol-6-yl}phenyl)urea Example 10A 2-(4-(4,4,5,5-tetramethyl-1,3,2-dioxaborolan-2-yl)-1H-pyrazol-1-yl)ethanol 4-(4,4,5,5-tetramethyl-1,3,2-dioxaborolan-2-yl)-1H-pyrazole (9.66 g, 49.8 mmol), 1,3-dioxolan-2-one (21 g, 238 mmol), and cesium carbonate (16 g, 49.1 mmol) were combined in a 100 mL round bottom flask At room temperature all reagents were solids. The reaction was warmed from room temperature to 100° C. in an oil bath, at which time the carbonate had melted and served as the solvent for the reaction, which then remained a slurry. After heating for 3.5 hours, the reaction was cooled to room temperature, diluted with ethyl acetate, and filtered through Celite® (diatomaceous earth) washing repeatedly with ethyl acetate. The filtrate was concentrated, and the residue was purified by chromatography on an Analogix® Intelliflash™ purification system using a SF60-200 g column at a flow rate of 80 mL/minute, eluting as follows: 5 minutes at 20% ethyl acetate/hexane, then ramped from 40% to 90% ethyl acetate/hexanes over 35 minutes, and then 100% ethyl acetate for another 20 minutes, to afford the title compound.

Example 10B

N-(3-fluorophenyl)-N'-(4-{3-[1-(2-hydroxyethyl)-1H-pyrazol-4-yl]-1H-indazol-6-yl}phenyl)urea The title compound was prepared as described in Example 1, substituting Example 10A for 1-methyl-4-(4,4,5,5-tetramethyl-1,3,2-dioxaborolan-2-yl)-1H-pyrazole in Example 1C. $^1$H NMR (300 MHz, DMSO-d$_6$) δ ppm 3.82 (dt, J=5.55, 5.16 Hz, 2 H) 4.25 (t, J=5.55 Hz, 2 H) 4.95 (t, J=5.16 Hz, 1 H) 6.80 (dt, J=8.33, 2.38 Hz, 1 H) 7.14 (d, J=7.93 Hz, 1 H) 7.32 (dd, J=7.93, 7.14 Hz, 1 H) 7.45 (d, J=8.72 Hz, 1 H) 7.52 (dt, J=11.90, 2.38 Hz, 1 H) 7.56-7.62 (m, 2 H) 7.66-7.74 (m, 3 H) 8.02 (s, 1 H) 8.06 (d, J=8.33 Hz, 1 H) 8.36 (s, 1 H) 8.87 (s, 1 H) 8.94 (s, 1 H) 12.94 (s, 1 H). MS (ESI(+)) m/e 457 (M+H)$^+$.

Example 11

N-(4-{3-[1-(2-hydroxyethyl)-1H-pyrazol-4-yl]-1H-indazol-6-yl}phenyl)-N'-[3-(trifluoromethyl)phenyl]urea The title compound was prepared as described in Example 1 except substituting 2-(4-(4,4,5,5-tetramethyl-1,3,2-dioxaborolan-2-yl)-1H-pyrazol-1-yl)ethanol and 1-isocyanato-3-(trifluoromethyl)benzene for 1-methyl-4-(4,4,5,5-tetramethyl-1,3,2-dioxaborolan-2-yl)-1H-pyrazole and 1-fluoro-3-isocyanatobenzene, respectively in Examples 1C and 1D. $^1$H NMR (300 MHz, DMSO-d$_6$) δ ppm 3.82 (dd, J=5.55, 5.16 Hz, 2 H) 4.25 (t, J=5.55 Hz, 2 H) 4.95 (t, J=5.16 Hz, 1 H) 7.32 (d, J=7.54 Hz, 1 H) 7.45 (d, J=8.33 Hz, 1 H) 7.49-7.57 (m, 1 H) 7.57-7.64 (m, 2 H) 7.66-7.74 (m, 3 H) 8.00-8.09 (m, 3 H) 8.36 (s, 1 H) 8.94 (s, 1 H) 9.10 (s, 1 H) 12.94 (s, 1 H).

Example 12

N-(4-{3-[1-(2-hydroxyethyl)-1H-pyrazol-4-yl]-1H-indazol-6-yl}phenyl)-N'-(3-methylphenyl)urea The title compound was prepared as described in Example 1 except substituting 2-(4-(4,4,5,5-tetramethyl-1,3,2-dioxaborolan-2-yl)-1H-pyrazol-1-yl)ethanol and 1-isocyanato-3-methylbenzene for 1-methyl-4-(4,4,5,5-tetramethyl-1,3,2-dioxaborolan-2-yl)-1H-pyrazole and 1-fluoro-3-isocyanatobenzene, respectively in Examples 1C and 1D. $^1$H NMR (300 MHz, DMSO-d$_6$) δ ppm 2.29 (s, 3 H) 3.82 (dt, J=5.95, 5.15 Hz, 2 H) 4.25 (t, J=5.95 Hz, 2 H) 4.95 (t, J=5.16 Hz, 1 H) 6.80 (d, J=7.14 Hz, 1 H) 7.17 (t, J=7.54 Hz, 1 H) 7.26 (d, J=8.72 Hz, 1 H) 7.32 (s, 1 H) 7.45 (d, J=8.73 Hz, 1 H) 7.55-7.62 (m, 2 H) 7.65-7.72 (m, 3 H) 8.02 (s, 1 H) 8.05 (d, J=8.33 Hz, 1 H) 8.35 (s, 1 H) 8.64 (s, 1 H) 8.80 (s, 1 H) 12.93 (s, 1 H). MS (ESI(+)) m/e 453 (M+H)$^+$.

Example 13

N-(3-fluorophenyl)-N'-{4-[3-(1-propyl-1H-pyrazol-4-yl)-1H-indazol-6-yl]phenyl}urea The title compound was prepared as described in Example 1 except substituting 1-propyl-4-(4,4,5,5-tetramethyl-1,3,2-dioxaborolan-2-yl)-1H-pyrazole for 1-methyl-4-(4,4,5,5-tetramethyl-1,3,2-dioxaborolan-2-yl)-1H-pyrazole in Example 1C. ¹H NMR (300 MHz, DMSO-d₆) δ ppm 0.89 (t, J=7.46 Hz, 3 H) 1.81-1.94 (m, 2 H) 4.16 (t, J=7.12 Hz, 2 H) 6.80 (t, J=10.51 Hz, 1 H) 7.15 (d, J=8.48 Hz, 1 H) 7.32 (t, J=8.14 Hz, 1 H) 7.44 (d, J=8.48 Hz, 1 H) 7.52 (d, J=11.87 Hz, 1 H) 7.55-7.63 (m, 2 H) 7.65-7.75 (m, 3 H) 8.01 (s, 1 H) 8.06 (d, J=8.48 Hz, 1 H) 8.40 (s, 1 H) 8.87 (s, 1 H) 8.94 (s, 1 H) 12.93 (s, 1 H). MS (ESI(+)) m/e 455 (M+H)⁺.

Example 14

N-(3-fluorophenyl)-N'-{4-[3-(1-methyl-1H-pyrazol-5-yl)-1H-indazol-6-yl]phenyl}urea The title compound was prepared as described in Example 1 except substituting 1-methyl-5-(4,4,5,5-tetramethyl-1,3,2-dioxaborolan-2-yl)-1H-pyrazole for 1-methyl-4-(4,4,5,5-tetramethyl-1,3,2-dioxaborolan-2-yl)-1H-pyrazole in Example 1C. ¹H NMR (300 MHz, DMSO-d₆) δ ppm 4.15 (s, 3 H) 6.79 (dt, J=8.72, 2.38 Hz, 1 H) 6.90 (d, J=1.98 Hz, 1 H) 7.14 (d, J=8.33 Hz, 1 H) 7.32 (dd, J=8.33, 6.74 Hz, 1 H) 7.48-7.56 (m, 2 H) 7.57-7.63 (m, 3 H) 7.69-7.75 (m, 2 H) 7.77 (s, 1 H) 7.96 (d, J=8.73 Hz, 1 H) 9.14 (s, 1 H) 9.23 (s, 1 H) 13.49 (s, 1 H). MS (ESI(+)) m/e 427 (M+H)⁺.

Example 15

N-(3-fluorophenyl)-N'-(4-{3-[1-(2-hydroxy-2-methylpropyl)-1H-pyrazol-4-yl]-1H-indazol-6-yl}phenyl)urea Example 15A 2-methyl-1-(4-(4,4,5,5-tetramethyl-1,3,2-dioxaborolan-2-yl)-1H-pyrazol-1-yl)propan-2-ol A mixture of 4-(4,4,5,5-tetramethyl-1,3,2-dioxaborolan-2-yl)-1H-pyrazole (500 mg, 2.57 mmol), Cs₂CO₃ (840 mg, 2.57 mmol) and 2,2-dimethyloxirane (2 mL) was heated in a sealed vial at 120° C. for 3 minutes with stirring in a Smith Synthesizer microwave (at 300 W), then allowed to cool and diluted with CH₂Cl₂. The resulting suspension was filtered, the filtrate was concentrated to afford the title compound.

Example 15B

The title compound was prepared as described in Example 1, substituting 2-methyl-1-(4-(4,4,5,5-tetramethyl-1,3,2-dioxaborolan-2-yl)-1H-pyrazol-1-yl)propan-2-ol for 1-methyl-4-(4,4,5,5-tetramethyl-1,3,2-dioxaborolan-2-yl)-1H-pyrazole in Example 1C. ¹H NMR (300 MHz, DMSO-d₆) δ ppm 1.12 (s, 6 H) 4.12 (s, 2 H) 4.75 (s, 1 H) 6.75-6.84 (m, 1 H) 7.11-7.18 (m, 1 H) 7.32 (dd, J=8.14, 7.12 Hz, 1 H) 7.42-7.62 (m, 4 H) 7.66-7.74 (m, 3 H) 7.99-8.06 (m, 2 H) 8.30 (s, 1 H) 8.87 (s, 1 H) 8.95 (s, 1 H) 12.95 (s, 1 H). MS (ESI(+)) m/e 485 (M+H)⁺.

Example 16

N-(3-fluorophenyl)-N'-{4-[3-(1-piperidin-4-yl-1H-pyrazol-4-yl)-1H-indazol-6-yl]phenyl}urea The title compound was prepared as a TFA salt as described in Example 1, substituting tert-butyl 4-(4-(4,4,5,5-tetramethyl-1,3,2-dioxaborolan-2-yl)-1H-pyrazol-1-yl)piperidine-1-carboxylate for 1-methyl-4-(4,4,5,5-tetramethyl-1,3,2-dioxaborolan-2-yl)-1H-pyrazole in Example 1C and the residue was purified via by preparative HPLC on a Waters Symmetry C8 column (25 mm×100 mm, 7 m particle size) using a gradient of 10% to 100% acetonitrile/0.1% aqueous TFA over 8 minutes (10 minute run time) at a flow rate of 40 mL/minutes. ¹H NMR (300 MHz, DMSO-d₆) δ ppm 2.12-2.36 (m, 4 H) 3.13 (dd, J=11.19 Hz, 2 H) 3.26-3.53 (m, 2 H) 4.54-4.67 (m, 1 H) 6.75-6.84 (m, 1 H) 7.15 (d, J=7.12 Hz, 1 H) 7.32 (dd, J=8.48, 6.78 Hz, 1 H) 7.43-7.48 (m, 1 H) 7.48-7.56 (m, 1 H) 7.56-7.64 (m, 2 H) 7.66-7.74 (m, 3 H) 8.08 (d, J=8.48 Hz, 1 H) 8.10 (s, 1 H) 8.34-8.50 (m, 1 H) 8.42 (s, 1H) 8.60-8.71 (m, 1 H) 8.97 (s, 1 H) 9.03 (s, 1 H) 12.99 (s, 1 H). MS (ESI(+)) m/e 496 (M+H)⁺.

Example 17

N-(3-methylphenyl)-N'-{3-[3-(1-methyl-1H-pyrazol-4-yl)-1H-indazol-6-yl]phenyl}urea The title compound was prepared as described in Example 1, substituting 3-(4,4,5,5-tetramethyl-1,3,2-dioxaborolan-2-yl)aniline and 1-isocyanato-3-methylbenzene for 4-(4,4,5,5-tetramethyl-1,3,2-dioxaborolan-2-yl)aniline and 1-fluoro-3-isocyanatobenzene respectively in Example 1D. ¹H NMR (300 MHz, DMSO-d₆) δ ppm 2.29 (s, 3 H) 3.94 (s, 3 H) 6.80 (d, J=7.46 Hz, 1 H) 7.16 (dd, J=8.14, 7.46 Hz, 1 H) 7.24 (d, J=8.14 Hz, 1 H) 7.32-7.46 (m, 5 H) 7.69 (s, 1 H) 7.93 (s, 1 H) 8.00 (s, 1 H) 8.08 (d, J=8.48 Hz, 1 H) 8.37 (s, 1 H) 8.62 (s, 1 H) 8.78 (s, 1 H) 12.98 (s, 1 H). MS (ESI(+)) m/e 423 (M+H)⁺.

Example 18

N-{4-[3-(1-methyl-1H-pyrazol-4-yl)-1H-indazol-6-yl]phenyl}-N'-[3-(trifluoromethyl)phenyl]urea The title compound was prepared as described in Examples 1C-1F, substituting 1-isocyanato-3-(trifluoromethyl)benzene for 1-fluoro-3-isocyanatobenzene. ¹H NMR (300 MHz, DMSO-d₆) δ ppm 3.94 (s, 3 H) 7.32 (d, J=7.46 Hz, 1 H) 7.43-7.48 (m, 1 H) 7.53 (t, J=7.80 Hz, 1 H) 7.57-7.64 (m, 3 H) 7.66-7.74 (m, 3 H) 7.98-8.07 (m, 3 H) 8.37 (s, 1 H) 9.11 (s, 1 H) 9.29 (s, 1 H) 12.97 (s, 1 H). MS (ESI(+)) m/e 475 (M+H)⁺.

Example 19

N-{4-[3-(1-methyl-1H-pyrazol-4-yl)-1H-indazol-6-yl]phenyl}-N'-[4-(trifluoromethyl)phenyl]urea The title compound was prepared as described in Examples 1C-1F, substituting 1-isocyanato-4-(trifluoromethyl)benzene for 1-fluoro-3-isocyanatobenzene. ¹H NMR (300 MHz, DMSO-d₆) δ ppm 3.94 (s, 3 H) 7.45 (d, J=8.33 Hz, 1 H) 7.57-7.74 (m, 9 H) 8.00 (s, 1H) 8.05 (d, J=8.73 Hz, 1 H) 8.38 (s, 1 H) 9.19 (s, 1 H) 9.41 (s, 1 H) 12.99 (s, 1 H). MS (ESI(+)) m/e 475 (M+H)⁺.

Example 20

N-(4-chlorophenyl)-N'-{4-[3-(1-methyl-1H-pyrazol-4-yl)-1H-indazol-6-yl]phenyl}urea The title compound was prepared as described in Examples 1C-1F, substituting 1-chloro-4-isocyanatobenzene for 1-fluoro-3-isocyanatobenzene. ¹H NMR (300 MHz, DMSO-d₆) δ ppm 3.94 (s, 3 H) 7.31-7.36 (m, 2 H) 7.42-7.47 (m, 1 H) 7.48-7.54 (m, 2 H) 7.56-7.61 (m, 2 H) 7.66-7.72 (m, 3 H) 7.99 (s, 1 H) 8.04 (d, J=8.48 Hz, 1 H) 8.37 (s, 1 H) 9.05 (s, 1 H) 9.08 (s, 1 H) 12.99 (s, 1 H). MS (ESI(+)) m/e 443 (M+H)⁺.

Example 21

N-(3-fluorophenyl)-N'-{4-[3-(1H-1,2,3-triazol-5-yl)-1H-indazol-6-yl]phenyl}urea

Example 21A 6-bromo-1-((2-(trimethylsilyl)ethoxy)methyl)-3-((trimethylsilyl)ethynyl)-1H-indazole To Example 1B (0.41 g, 0.905 mmol) and copper(I) iodide (10 mg, 0.053 mmol) under argon was added terahydrofuran (25 ml) and triethylamine (1.261 ml, 9.05 mmol) and then ethynyltrimethylsilane (0.153 ml, 1.086 mmol) and [1,1'-bis(diphenylphosphino)ferrocene]dichloropalladium(II) (0.037 g, 0.045 mmol). The resulting suspension was stirred at room temperature for 16 hours, then partitioned between ethyl acetate and dilute NaHCO₃ solution. The organic extract was dried with MgSO₄, concentrated and the residue was purified via silica gel chromatography eluting with ethyl acetate/hexanes to afford the title compound.

Example 21B 1-(3-fluorophenyl)-3-(4-(1-((2-(trimethylsilyl)ethoxy)methyl)-3-((trimethylsilyl)ethynyl)-1H-indazol-6-yl)phenyl)urea The title compound was prepared by substituting Example 21A for Example 1C in Example 1E.

Example 21C 1-(4-(3-ethynyl-1-((2-(trimethylsilyl)ethoxy)methyl)-1H-indazol-6-yl)phenyl)-3-(3-fluorophenyl)urea A solution of Example 21B (660 mg) in 50 ml methanol was treated with excess K₂CO₃, stirred at 50° C. for 1 hour, then concentrated to ca. 2 mL and partitioned between ethyl acetate and brine. The aqueous layer was back extracted with ethyl acetate, the combined organic extracts were dried (MgSO₄) and concentrated and the residue was purified via silica gel chromatography eluting with 0 to 0.75% methanol in CH₂Cl₂. to afford the title compound.

Example 21D 1-(4-(3-(1H-1,2,3-triazol-5-yl)-1-((2-(trimethylsilyl)ethoxy)methyl)-1H-indazol-6-yl)phenyl)-3-(3-fluorophenyl)urea A solution of Example 21C (90 mg, 0.180 mmol) in N,N-dimethylformamide (4 ml) and methanol (0.7 ml) under argon was treated with Cu(I)I (5.00 mg, 0.026 mmol) and trimethylsilyl azide (0.249 ml, 1.798 mmol), then heated at 100° C. in an oil bath in a sealed tube for 3 hours. An additional amount of trimethylsilyl azide (0.5 ml) was added and the vial was recapped and heated at 100° C. for 4 hours and then stirred at room temperature for 16 hours. The resulting mixture was partitioned between ethyl acetate and brine, and the organic extract was dried with MgSO₄, concentrated and the residue was purified on a 12 gram Silicycle column eluting with 2 to 3% methanol in CH₂Cl₂ to afford the title compound.

Example 21E

N-(3-fluorophenyl)-N'-{4-[3-(1H-1,2,3-triazol-5-yl)-1H-indazol-6-yl]phenyl}urea

The title compound was prepared by substituting Example 21D for 1E in Example 1F. $^1$H NMR (300 MHz, DMSO-d$_6$) δ ppm 6.79 (dt, J=8.14, 2.71 Hz, 1 H) 7.15 (d, J=8.14 Hz, 1H) 7.32 (dd, J=8.14, 6.78 Hz, 1 H) 7.48-7.56 (m, 2 H) 7.57-7.65 (m, 2 H) 7.69-7.76 (m, 3H) 8.26 (d, J=8.48 Hz, 1 H) 8.35 (s, 1 H) 9.08 (s, 1 H) 9.16 (s, 1 H) 13.18-13.52 (bs, 1 H). MS (ESI(+)) m/e 414 (M+H)⁺.

Example 22

N-(3-chlorophenyl)-N'-{4-[3-(1-methyl-1H-pyrazol-4-yl)-1H-indazol-6-yl]phenyl}urea The title compound was prepared as described in Examples 1C-1F, substituting 1-chloro-3-isocyanatobenzene for 1-fluoro-3-isocyanatobenzene. $^1$H NMR (300 MHz, DMSO-d$_6$) δ ppm 3.94 (s, 3 H) 7.00-7.05 (m, 1 H) 7.28-7.33 (m, 2 H) 7.45 (d, J=8.72 Hz, 1 H) 7.56-7.62 (m, 2 H) 7.66-7.75 (m, 4 H) 8.00 (s, 1 H) 8.05 (d, J=8.72 Hz, 1 H) 8.38 (s, 1 H) 9.11 (s, 1 H) 9.18 (s, 1 H) 12.97 (s, 1 H). MS (ESI(+)) m/e 443 (M+H)⁺.

Example 23

N-(2-chlorophenyl)-N'-{4-[3-(1-methyl-1H-pyrazol-4-yl)-1H-indazol-6-yl]phenyl}urea The title compound was prepared as described in Examples 1C-1F, substituting 1-chloro-2-isocyanatobenzene for 1-fluoro-3-isocyanatobenzene. $^1$H NMR (300 MHz, DMSO-d$_6$) δ ppm 3.94 (s, 3 H) 7.01-7.08 (m, 1 H) 7.28-7.35 (m, 1 H) 7.43-7.50 (m, 2 H) 7.58-7.64 (m, 2 H) 7.66-7.75 (m, 3 H) 7.99 (s, 1 H) 8.05 (d, J=8.48 Hz, 1 H) 8.16-8.22 (m, 1 H) 8.38 (s, 1 H) 8.39 (s, 1 H) 9.63 (s, 1 H) 12.97 (s, 1 H). MS (ESI(+)) m/e 443 (M+H)⁺.

Example 24

N-(3-fluorophenyl)-N'-{4-[3-(1-methyl-1H-pyrazol-4-yl)-1H-indazol-6-yl]benzyl}urea The title compound was prepared as described in Examples 1D-1F, substituting (4-(4,4,5,5-tetramethyl-1,3,2-dioxaborolan-2-yl)phenyl)methanamine for 4-(4,4,5,5-tetramethyl-1,3,2-dioxaborolan-2-yl)aniline. $^1$H NMR (300 MHz, DMSO-d$_6$) δ ppm 3.94 (s, 3 H) 4.37 (d, J=3.97 Hz, 2 H) 6.70 (td, J=8.72, 2.38 Hz, 1 H) 6.80-6.90 (m, 1 H) 7.07 (d, J=7.54 Hz, 1 H) 7.25 (dd, J=7.93, 7.14 Hz, 1 H) 7.40-7.49 (m, 3 H) 7.49-7.53 (m, 1 H) 7.68-7.75 (m, 3 H) 8.00 (s, 1 H) 8.07 (d, J=8.33 Hz, 1 H) 8.37 (s, 1 H) 8.97 (s, 1 H) 12.98 (s, 1 H). MS (ESI(+)) m/e 441 (M+H)⁺.

Example 25

N-{4-[3-(1-methyl-1H-pyrazol-4-yl)-1H-indazol-6-yl]phenyl}-N'-[3-(trifluoromethoxy)phenyl]urea The title compound was prepared as described in Examples 1C-1F, substituting 1-isocyanato-3-(trifluoromethoxy)benzene for 1-fluoro-3-isocyanatobenzene. $^1$H NMR (300 MHz, DMSO-d$_6$) δ ppm 3.94 (s, 3 H) 6.95 (d, J=7.93 Hz, 1 H) 7.32 (d, J=8.73 Hz, 1 H) 7.43 (dd, J=15.86, 7.93 Hz, 4 H) 7.57-7.63

(m, 2 H) 7.66-7.74 (m, 4 H) 7.99 (s, 1 H) 8.05 (d, J=8.73 Hz, 1 H) 8.38 (s, 1 H) 9.09 (s, 1 H) 9.27 (s, 1 H) 12.98 (s, 1 H). MS (ESI(+)) m/e 493 (M+H)+.

Example 26

N-{4-[3-(1-methyl-1H-pyrazol-4-yl)-1H-indazol-6-yl]phenyl}-N'-[2-(trifluoromethyl)phenyl]urea The title compound was prepared as described in Examples 1C-1F, substituting 1-isocyanato-2-(trifluoromethyl)benzene for 1-fluoro-3-isocyanatobenzene. $^1$H NMR (300 MHz, DMSO-$d_6$) δ ppm 3.94 (s, 3 H) 7.30 (t, J=7.54 Hz, 1 H) 7.45 (d, J=8.73 Hz, 1 H) 7.57-7.75 (m, 7 H) 7.97 (d, J=7.93 Hz, 1 H) 8.00 (s, 1 H) 8.05 (d, J=8.33 Hz, 2 H) 8.16 (s, 1 H) 8.38 (s, 1 H) 9.58 (s, 1 H) 13.00 (s, 1 H). MS (ESI(+)) m/e 477 (M+H)+.

Example 27

N-{4-[3-(1-methyl-1H-pyrazol-4-yl)-1H-indazol-6-yl]phenyl}-N'-[2-(trifluoromethoxy)phenyl]urea The title compound was prepared as described in Examples 1C-1F, substituting 1-isocyanato-2-(trifluoromethoxy)benzene for 1-fluoro-3-isocyanatobenzene. $^1$H NMR (300 MHz, DMSO-$d_6$) δ ppm 3.94 (s, 3 H) 7.11 (t, J=7.93 Hz, 1 H) 7.32-7.42 (m, 2 H) 7.45 (d, J=8.33 Hz, 1 H) 7.57-7.64 (m, 2 H) 7.67-7.75 (m, 3 H) 8.00 (s, 1 H) 8.05 (d, J=8.33 Hz, 1H) 8.29 (d, J=8.33 Hz, 1 H) 8.38 (s, 1 H) 8.52 (s, 1 H) 9.44 (s, 1 H) 12.95 (s, 1 H). MS (ESI(+)) m/e 493 (M+H)+.

Example 28

N-{4-[3-(1-methyl-1H-pyrazol-4-yl)-1H-indazol-6-yl]phenyl}-N'-[4-(trifluoromethoxy)phenyl]urea The title compound was prepared as described in Examples 1C-1F, substituting 1-isocyanato-4-(trifluoromethoxy)benzene for 1-fluoro-3-isocyanatobenzene. $^1$H NMR (300 MHz, DMSO-$d_6$) δ ppm 3.94 (s, 3 H) 7.30 (d, J=8.48 Hz, 2 H) 7.45 (d, J=8.48 Hz, 1 H) 7.55-7.62 (m, 4 H) 7.65-7.73 (m, 3 H) 7.99 (s, 1 H) 8.04 (d, J=8.48 Hz, 1 H) 8.37 (s, 1 H) 9.05 (s, 1 H) 9.13 (s, 1 H) 12.98 (s, 1 H). MS (ESI(+)) m/e 493 (M+H)+.

Example 29

N-(3-fluorophenyl)-N'-{3-[3-(1-methyl-1H-pyrazol-4-yl)-1H-indazol-6-yl]benzyl}urea The title compound was prepared as described in Examples 1D-1F, substituting (3-(4,4,5,5-tetramethyl-1,3,2-dioxaborolan-2-yl)phenyl)methanamine for 4-(4,4,5,5-tetramethyl-1,3,2-dioxaborolan-2-yl)aniline. $^1$H NMR (300 MHz, DMSO-$d_6$) δ ppm 3.94 (s, 3 H) 4.41 (d, J=5.76 Hz, 2 H) 6.70 (td, J=8.14, 3.39 Hz, 1 H) 6.83 (t, J=5.76 Hz, 1 H) 7.06 (d, J=9.15 Hz, 1 H) 7.24 (dd, J=8.14, 7.12 Hz, 1 H) 7.34 (d, J=7.80 Hz, 1 H) 7.42-7.51 (m, 3 H) 7.60-7.72 (m, 3 H) 8.00 (s, 1 H) 8.08 (d, J=8.48 Hz, 1 H) 8.38 (s, 1 H) 8.89 (s, 1 H) 12.99 (s, 1 H). MS (ESI(+)) m/e 441 (M+H)+.

Example 30

N-(5-methylisoxazol-3-yl)-N'-{4-[3-(1-methyl-1H-pyrazol-4-yl)-1H-indazol-6-yl]phenyl}urea The title compound was prepared as described in Examples 1E-1F, substituting 1-(5-methylisoxazol-3-yl)-3-(4-(4,4,5,5-tetramethyl-1,3,2-dioxaborolan-2-yl)phenyl)urea for Example 1D. $^1$H NMR (300 MHz, DMSO-$d_6$) δ ppm 2.37 (s, 3 H) 3.94 (s, 3 H) 6.57-6.57 (m, 1 H) 7.45 (d, J=8.48 Hz, 1 H) 7.55-7.61 (m, 2 H) 7.66-7.74 (m, 3 H) 8.00 (s, 1 H) 8.05 (d, J=8.81 Hz, 1 H) 8.38 (s, 1 H) 9.19 (s, 1 H) 9.58 (s, 1 H) 12.98 (s, 1 H). MS (ESI(+)) m/e 414 (M+H)+.

Example 31

3-fluoro-N-{4-[3-(1-methyl-1H-pyrazol-4-yl)-1H-indazol-6-yl]benzyl}benzamide

Example 31A tert-butyl 4-(1-((2-(tert-butylsilyl)ethoxy)methyl)-3-(1-methyl-1H-pyrazol-4-yl)-1H-indazol-6-yl)benzyl-carbamate The title compound was prepared as described in Example 1E, substituting tert-butyl 4-(4,4,5,5-tetramethyl-1,3,2-dioxaborolan-2-yl)benzylcarbamate for Example 1D.

Example 31B (4-(3-(1-methyl-1H-pyrazol-4-yl)-1H-indazol-6-yl)phenyl)methanamine A solution of Example 31A (0.17 g, 0.319 mmol) in CH$_2$Cl$_2$ (4 mL) under argon was treated with trifluoroacetic acid (1 ml, 12.98 mmol), stirred at room temperature for 1 hour, then partitioned between dilute Na$_2$CO$_3$ solution and ethyl acetate (2×). The combined organics were dried (MgSO$_4$), then concentrated to afford the title compound which was used as is in the next step.

Example 31C 3-fluoro-N-{4-[3-(1-methyl-1H-pyrazol-4-yl)-1H-indazol-6-yl]benzyl}benzamide A 0° C. suspension of Example 31B (70 mg, 0.231 mmol) in tetrahydrofuran (15 ml) was treated with triethylamine (1.00 ml, 7.17 mmol) followed by 3-fluorobenzoyl chloride (0.014 ml, 0.115 mmol) added dropwise. The reaction was allowed to warm to room temperature slowly and after 2 hours was treated with an additional 14 uL acid chloride, stirred for 18 hours, then partitioned between brine and ethyl acetate. The organic extract was dried with MgSO$_4$, concentrated and the residue was purified via by preparative HPLC on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/minute to afford the title compound. $^1$H NMR (300 MHz, DMSO-$d_6$) δ ppm 3.94 (s, 3 H) 4.55 (d, J=5.95 Hz, 2 H) 7.35-7.81 (m, 10 H) 7.99 (s, 1 H) 8.06 (d, J=8.33 Hz, 1 H) 8.37 (s, 1 H) 9.19 (t, J=5.95 Hz, 1 H) 12.98 (s, 1 H). MS (ESI(+)) m/e 426 (M+H)+.

Example 32

N-(3-methylphenyl)-N'-[4-(3-phenyl-1H-indazol-6-yl)phenyl]urea

The title compound was prepared as described in Examples 1C-1F, substituting phenylboronic acid and 1-isocyanato-3-methylbenzene for 1-methyl-4-(4,4,5,5-tetramethyl-1,3,2-dioxaborolan-2-yl)-1H-pyrazole and 1-fluoro-3-isocyanatobenzene, respectively. ¹H NMR (300 MHz, DMSO-d₆) δ ppm 2.29 (s, 3 H) 6.80 (d, J=7.14 Hz, 1 H) 7.17 (t, J=7.54 Hz, 1 H) 7.26 (d, J=8.73 Hz, 1 H) 7.32 (s, 1 H) 7.42 (t, J=7.54 Hz, 1 H) 7.49-7.55 (m, 3 H) 7.57 (d, J=3.97 Hz, 1 H) 7.61 (s, 1 H) 7.69 (s, 1 H) 7.72 (s, 1 H) 7.75 (s, 1 H) 8.01 (s, 1 H) 8.04 (s, 1 H) 8.12 (d, J=8.73 Hz, 1 H) 8.63 (s, 1 H) 8.80 (s, 1 H) 13.26 (s, 1 H). MS (ESI(−)) m/e 417 (M−H).

Example 33

N-(3-methylphenyl)-N'-[4-(3-pyridin-3-yl-1H-indazol-6-yl)phenyl]urea

The title compound was prepared as an HCl salt as described in Examples 1C-1F, substituting pyridin-3-ylboronic acid and 1-isocyanato-3-methylbenzene for 1-methyl-4-(4,4,5,5-tetramethyl-1,3,2-dioxaborolan-2-yl)-1H-pyrazole and 1-fluoro-3-isocyanatobenzene, respectively. ¹H NMR (300 MHz, DMSO-d₆) δ ppm 2.29 (s, 3 H) 6.80 (d, J=7.12 Hz, 1 H) 7.17 (t, J=7.46 Hz, 1 H) 7.27 (d, J=8.82 Hz, 1 H) 7.32 (s, 1 H) 7.60 (m, 3H) 7.71 (s, 1 H) 7.74 (s, 1 H) 7.81 (s, 1 H) 7.86 (dd, J=5.43, 2.37 Hz, 1H) 8.20 (s, 1 H) 8.23 (s, 1 H) 8.76 (m, 2 H) 8.92 (s, 1 H) 9.12 (s, 1 H) 9.35 (s, 1 H) 13.66 (s, 1H). MS (ESI(+)) m/e 420 (M+H)⁺.

Example 34

N-(3-methylphenyl)-N'-[3-(3-pyridin-3-yl-1H-indazol-6-yl)phenyl]urea

Example 34A 1-(3-(4,4,5,5-tetramethyl-1,3,2-dioxaborolan-2-yl)phenyl)-3-m-tolylurea The title compound was prepared by substituting 3-(4,4,5,5-tetramethyl-1,3,2-dioxaborolan-2-yl)aniline and 1-isocyanato-3-methylbenzene for 4-(4,4,5,5-tetramethyl-1,3,2-dioxaborolan-2-yl)aniline and 1-fluoro-3-isocyanatobenzene, respectively in Example 1D.

Example 34B

N-(3-methylphenyl)-N'-[3-(3-pyridin-3-yl-1H-indazol-6-yl)phenyl]urea

The title compound was prepared as described in Examples 1C-F, substituting pyridin-3-ylboronic acid and Example 34A for 1-methyl-4-(4,4,5,5-tetramethyl-1,3,2-dioxaborolan-2-yl)-1H-pyrazole and Example 1D, respectively. ¹H NMR (300 MHz, DMSO-d₆) δ ppm 2.29 (s, 3 H) 6.80 (d, J=7.12 Hz, 1 H) 7.17 (t, J=7.46 Hz, 1 H) 7.25 (d, J=8.82 Hz, 1 H) 7.34 (s, 1H) 7.41 (m, 3 H) 7.57 (dd, J=1.36, 7.12 Hz, 1 H) 7.83 (m, 2H) 7.99 (s, 1H) 8.26 (d, J=8.48 Hz, 1 H) 8.73 (m, 2 H) 8.79 (s, 1 H) 8.96 (s, 1 H) 9.35 (s, 1 H) 13.68 (s, 1H). MS (ESI(+)) m/e 420 (M+H)⁺.

Example 35

N-(3-methylphenyl)-N'-{4-[3-(1,3-thiazol-4-yl)-1H-indazol-6-yl]phenyl}urea

The title compound was prepared as described in Examples 1C-1F, substituting 4-(4,4,5,5-tetramethyl-1,3,2-dioxaborolan-2-yl)thiazole and 1-isocyanato-3-methylbenzene for 1-methyl-4-(4,4,5,5-tetramethyl-1,3,2-dioxaborolan-2-yl)-1H-pyrazole and 1-fluoro-3-isocyanatobenzene, respectively. ¹H NMR (300 MHz, DMSO-d₆) δ ppm 2.29 (s, 3 H) 6.80 (d, J=7.14 Hz, 1 H) 7.17 (t, J=7.14, 7.93 Hz, 1 H) 7.26 (d, J=7.93 Hz, 1 H) 7.32 (s, 1 H) 7.52 (dd, J=1.19, 8.33 Hz, 1 H) 7.57 (s, 1 H) 7.60 (s, 1 H) 7.69 (s, 1H) 7.73 (s, 2H) 8.17 (d, J=1.59 Hz, 1 H) 8.37 (d, J=8.33 Hz, 1 H) 8.71 (s, 1 H) 8.88 (s, 1H) 9.32 (d, J=1.98 Hz, 1H) 13.28 (bs, 1 H). MS (ESI(+)) m/e 426 (M+H)⁺.

Example 36

N-{4-[3-(1H-indol-2-yl)-1H-indazol-6-yl]phenyl}-N'-(3-methylphenyl)urea

Example 36A tert-butyl 2-(6-(4-(3-m-tolylureido)phenyl)-142-(trimethylsilyl)ethoxy)methyl)-1H-indazol-3-yl)-1H-indole-1-carboxylate The title compound was prepared as described in Examples 1C-1E, substituting 1-(tert-butoxycarbonyl)-1H-indol-2-ylboronic acid and 1-isocyanato-3-methylbenzene for 1-methyl-4-(4,4,5,5-tetramethyl-1,3,2-dioxaborolan-2-yl)-1H-pyrazole and 1-fluoro-3-isocyanatobenzene, respectively.

Example 36B

N-{4-[3-(1H-indol-2-yl)-1H-indazol-6-yl]phenyl}-N'-(3-methylphenyl)urea

A solution of Example 36A (54.3 mg, 0.079 mmol), ethylenediamine (0.053 ml, 0.789 mmol) and tetrabutylammonium fluoride (3.16 ml, 3.16 mmol) in tetrahydrofuran in a 10 ml microwave tube was placed in a Biotage microwave at 110° for 90 minutes. The reaction solution was diluted with water and extracted two times with ethyl acetate and the organics were combined, dried over MgSO₄, and filtered. The filtrate was concentrated, and purified using a SF40-240 g column (~317 ml void) at 47% max pump rate (~85 ml/min) with 3% methanol/CH₂Cl₂ to give the title compound. ¹H NMR (300 MHz, DMSO-d₆) δ ppm 2.29 (s, 3 H) 6.80 (d, J=7.14 Hz, 1 H) 7.02 (m, 1H) 7.12 (m, 2 H) 7.18 (d, J=7.54 Hz, 1 H) 7.26 (d, J=8.73 Hz, 1 H) 7.33 (s, 1 H) 7.46 (d, J=7.93 Hz, 1H) 7.55 (dd, J=1.19, 8.72 Hz, 1 H) 7.59 (s, 1 H) 7.62 (s, 2H) 7.71 (s, 1 H) 7.74 (d, J=3.97 Hz, 2H) 8.24 (d, J=8.33 Hz, 1 H) 8.70 (s, 1H) 8.87 (s, 1 H) 11.59 (d, J=1.19 Hz, 1H) 13.33 (s, 1 H). MS (ESI(+)) m/e 458 (M+H)⁺.

Example 37

2-(4-{6-[4-({[(3-fluorophenyl)amino]carbonyl}amino)phenyl]-1H-indazol-3-yl}-1H-pyrazol-1-yl)-N-methylpropanamide Example 37A N-methyl-2-(4-(4,4,5,5-tetramethyl-1,3,2-dioxaborolan-2-yl)-1H-pyrazol-1-yl)propanamide A suspension of 4-(4,4,5,5-tetramethyl-1,3,2-dioxaborolan-2-yl)-1H-pyrazole (5.29 g, 27.3 mmol), 2-bromo-N-methylpropanamide (9.05 g, 54.5 mmol) and potassium carbonate (5.65 g, 40.9 mmol) in 136 ml acetone was refluxed for 68 hours. The white suspension was filtered through Celite with acetone washes; and the filtrate was concentrated and purified via silica gel chromatography (80 mm; 1 L 65% ethyl acetate/hexanes to 80% ethyl acetate/hexanes) to afford the title compound.

Example 37B 2-(4-{6-[4-({[(3-fluorophenyl)amino]carbonyl}amino)phenyl]-1H-indazol-3-yl}-1H-pyrazol-1-yl)-N-methylpropanamide The title compound was prepared as described in Example 1, substituting N-methyl-2-(4-(4,4,5,5-tetramethyl-1,3,2-dioxaborolan-2-yl)-1H-pyrazol-1-yl)propanamide for 1-methyl-4-(4,4,5,5-tetramethyl-1,3,2-dioxaborolan-2-yl)-1H-pyrazole. $^1$H NMR (300 MHz, DMSO-d$_6$) δ ppm 1.69 (d, J=7.14 Hz, 3 H) 2.63 (d, J=4.76 Hz, 3 H) 5.07 (q, J=7.14 Hz, 1 H) 6.79 (dt, J=8.33, 1.98 Hz, 1 H) 7.14 (d, J=9.52 Hz, 1 H) 7.32 (dd, J=8.33, 7.14 Hz, 1 H) 7.46 (d, J=8.33 Hz, 1 H) 7.52 (d, J=11.90 Hz, 1 H) 7.56-7.74 (m, 5 H) 8.03-8.13 (m, 3 H) 8.42 (s, 1 H) 9.08 (s, 1 H) 9.16 (s, 1 H) 13.01 (s, 1 H). MS (ESI(+)) m/e 498 (M+H)$^+$.

Example 38

N-methyl-2-[4-(6-{4-[(phenylsulfonyl)amino]phenyl}-1H-indazol-3-yl)-1H-pyrazol-1-yl]propanamide The title compound was prepared as described in Example 1, substituting Example 37A for 1-methyl-4-(4,4,5,5-tetramethyl-1,3,2-dioxaborolan-2-yl)-1H-pyrazole and N-(4-(4,4,5,5-tetramethyl-1,3,2-dioxaborolan-2-yl)phenyl)benzenesulfonamide (J. Med. Chem. 2007, 50, 1584) for Example 1D. $^1$H NMR (300 MHz, DMSO-d$_6$) δ ppm 1.68 (d, J=7.14 Hz, 3 H) 2.62 (d, J=4.36 Hz, 3 H) 5.06 (q, J=7.14 Hz, 1 H) 7.22 (d, J=8.72 Hz, 2 H) 7.38 (d, J=8.72 Hz, 1 H) 7.53-7.67 (m, 6 H) 7.79-7.85 (m, 2 H) 8.00-8.08 (m, 3 H) 8.39 (s, 1 H) 10.45 (s, 1 H) 12.99 (s, 1 H). MS (ESI(+)) m/e 501 (M+H)$^+$.

Example 39

3-fluoro-N-{4-[3-(1-methyl-1H-pyrazol-4-yl)-1H-indazol-6-yl]phenyl}benzamide

The title compound was prepared as described in Example 1, substituting 3-fluoro-N-(4-(4,4,5,5-tetramethyl-1,3,2-dioxaborolan-2-yl)phenyl)benzamide (prepared by substituting 4-(4,4,5,5-tetramethyl-1,3,2-dioxaborolan-2-yl)aniline for Example 31B in Example 31C) for Example 1D. $^1$H NMR (300 MHz, DMSO-d$_6$) δ ppm 3.94 (s, 3 H) 7.43-7.51 (m, 2 H) 7.57-7.66 (m, 1 H) 7.72 (s, 1 H) 7.75-7.89 (m, 5 H) 7.93 (d, J=8.82 Hz, 2 H) 8.01 (s, 1 H) 8.07 (d, J=9.16 Hz, 1 H) 8.39 (s, 1 H) 10.45 (s, 1 H). MS (ESI(+)) m/e 412 (M+H)$^+$.

Example 40

N-{4-[3-(1-methyl-1H-pyrazol-4-yl)-1H-indazol-6-yl]phenyl}-N'-[3-(pyrrolidin-1-ylmethyl)phenyl]urea The title compound was prepared as described in Example 1, substituting 3-(pyrrolidin-1-ylmethyl)aniline and 2-(4-isocyanatophenyl)-4,4,5,5-tetramethyl-1,3,2-dioxaborolane for 4-(4,4,5,5-tetramethyl-1,3,2-dioxaborolan-2-yl)aniline and 1-fluoro-3-isocyanatobenzene, respectively in Example 1D. $^1$H NMR (300 MHz, DMSO-d$_6$) δ ppm 1.81-1.94 (m, 2 H) 1.98-2.12 (m, 2 H) 3.04-3.18 (m, 2 H) 3.34-3.46 (m, 2 H) 3.94 (s, 3 H) 4.35 (d, J=5.55 Hz, 2 H) 7.12 (d, J=6.35 Hz, 1 H) 7.35-7.48 (m, 3 H) 7.58-7.74 (m, 5 H) 7.81 (s, 1 H) 7.99 (s, 1 H) 8.05 (d, J=8.73 Hz, 1 H) 8.37 (s, 1 H) 9.03 (s, 1 H) 9.06 (s, 1H) 9.77 (s, 1 H) 12.95 (s, 1 H). MS (ESI(+)) m/e 492 (M+H)$^+$.

Example 41

N-(3-fluorophenyl)-N'-(4-{3-[1-(2-pyrrolidin-1-ylethyl)-1H-pyrazol-4-yl]-1H-indazol-6-yl}phenyl)urea Example 41A 6-bromo-3-(1-(2-(pyrrolidin-1-yl)ethyl)-1H-pyrazol-4-yl)-1-((2-(trimethylsilyl)ethoxy)methyl)-1H-indazole Sodium hydride (17.46 mg, 0.437 mmol) was added in a single portion to a solution of 6-bromo-3-(1H-pyrazol-4-yl)-1-((2-(trimethylsilyl)ethoxy)methyl)-1H-indazole (101 mg, 0.257 mmol) (prepared by substituting 4-(4,4,5,5-tetramethyl-1,3,2-dioxaborolan-2-yl)-1H-pyrazole for 1-methyl-4-(4,4,5,5-tetramethyl-1,3,2-dioxaborolan-2-yl)-1H-pyrazole in Example 1C) in DMF (10 ml) at room temperature under argon. The resulting bubbling solution was stirred for 20 minutes, then treated with 1-(2-chloroethyl)pyrrolidine (51.5 mg, 0.385 mmol) which was dissolved in 0.5 ml DMF and added dropwise via pipette. The resulting mixture was stirred at 70° C. for 3 hours, allowed to cool, and partitioned between ethyl acetate and water. The organic extract was washed with brine, dried with MgSO$_4$, and filtered. The filtrate was concentrated and the residue was purified via silica gel chromatography eluting with 3 to 5% CH$_2$Cl$_2$/CH$_3$OH to give the title compound.

Example 41B

N-(3-fluorophenyl)-N'-(4-{3-[1-(2-pyrrolidin-1-ylethyl)-1H-pyrazol-4-yl]-1H-indazol-6-yl}phenyl)urea The title compound was prepared as described in Example 1C-1F, substituting Example 41A for Example 1C. $^1$H NMR (300 MHz, DMSO-d$_6$) δ ppm 1.80-1.93 (m, 2 H) 1.95-2.09 (m, 2 H) 3.00-3.15 (m, 2 H) 3.51-3.65 (m, 2 H) 3.70-3.80 (m, 2 H) 4.61 (t, J=5.95 Hz, 2 H) 6.75-6.84 (m, 1 H) 7.15 (d, J=7.93 Hz, 1 H) 7.32 (dd, J=8.33, 7.14 Hz, 1 H) 7.44-7.56 (m, 2 H) 7.56-7.64 (m, 2 H) 7.67-7.74 (m, 3 H) 8.07 (d, J=8.33 Hz, 1 H) 8.15 (s, 1 H) 8.54 (s, 1 H) 8.98 (s, 1 H) 9.04 (s, 1 H) 9.56 (s, 1 H) 13.02 (s, 1 H). MS (ESI(+)) m/e 510 (M+H)$^+$.

Example 42

N-{4-[3-(1H-indol-3-yl)-1H-indazol-6-yl]phenyl}-N'-(3-methylphenyl)urea

The title compound was prepared as described in Examples 1C-1E, followed by Example 36B, substituting 1-(phenylsulfonyl)-1H-indol-3-ylboronic acid and 1-isocyanato-3-methylbenzene for 1-methyl-4-(4,4,5,5-tetramethyl-1,3,2-dioxaborolan-2-yl)-1H-pyrazole and 1-fluoro-3-isocyanatobenzene, respectively. $^1$H NMR (300 MHz, DMSO-d$_6$) δ ppm 2.29 (s, 3 H) 6.80 (d, J=7.54 Hz, 1 H) 7.08-7.23 (m, 3 H) 7.26 (d, 1H, J=8.33 Hz) 7.33 (s, 1H) 7.42-7.50 (m, 2H) 7.58 (s, 1H) 7.61 (s, 2H) 7.70 (s, 2H) 7.73 (s, 1H) 8.14 (d, J=2.38 Hz, 1H) 8.17 (d, J=8.33 Hz, 1 H) 8.35

(d, J=7.54 Hz, 1H) 8.71 (s, 1H) 8.87 (s, 1 H) 11.44 (s, 1H) 12.93 (s, 1 H). MS (ESI(+)) m/e 458 (M+H)+.

Example 43

N-[4-(3-{1-[(2R)-2-hydroxypropyl]-1H-pyrazol-4-yl}-1H-indazol-6-yl)phenyl]-N'-(3-methylphenyl)urea The title compound was prepared as in Examples 1C-1F, substituting (R)-1-(3-(4,4,5,5-tetramethyl-1,3,2-dioxaborolan-2-yl)-1H-pyrazol-1-yl)propan-2-ol and 1-isocyanato-3-methylbenzene for 1-methyl-4-(4,4,5,5-tetramethyl-1,3,2-dioxaborolan-2-yl)-1H-pyrazole and 1-fluoro-3-isocyanatobenzene, respectively. $^1$H NMR (300 MHz, DMSO-d$_6$) δ ppm 1.06-1.12 (m, 3H) 2.29 (s, 3H) 4.03-4.14 (m, 3H) 4.96 (d, J=4.75 Hz, 1H) 6.80 (d, J=7.46 Hz, 1 H) 7.17 (t, J=7.46, 8.14 Hz, 1 H) 7.25 (d, J=8.82 Hz, 1 H) 7.32 (s, 1 H) 7.45 (dd, J=8.82, 1.36 Hz, 1 H) 7.57 (s, 1 H) 7.60 (s, 1H) 7.67 (s, 2 H) 7.71 (s, 1H) 8.02 (d, J=3.05 Hz, 1H) 8.06 (s, 1H) 8.33 (s, 1 H) 8.61 (s, 1 H) 8.77 (s, 1 H) 12.93 (s, 1 H). MS (ESI(+)) m/e 467 (M+H)+.

Example 44

3-fluoro-N-{3-[3-(1-methyl-1H-pyrazol-4-yl)-1H-indazol-6-yl]phenyl}benzamide

The title compound was prepared as described in Example 1, substituting 3-fluoro-N-(3-(4,4,5,5-tetramethyl-1,3,2-dioxaborolan-2-yl)phenyl)benzamide (prepared by substituting 3-(4,4,5,5-tetramethyl-1,3,2-dioxaborolan-2-yl)aniline for Example 31B in Example 31C) for Example 1D. $^1$H NMR (300 MHz, DMSO-d$_6$) δ ppm 3.95 (s, 3 H) 7.44 (d, J=1.19 Hz, 1H) 7.47 (d, J=1.19, 1H) 7.48-7.55 (m, 2H) 7.57-7.67 (m, 1H) 7.72 (s, 1 H) 7.79-7.90 (m, 3H) 8.01 (s, 1H) 8.11 (d, J=8.33 Hz, 1 H) 8.20 (s, 1 H) 8.39 (s, 1 H) 10.43 (s, 1H) 13.02 (s, 1 H). MS (ESI(+)) m/e 412 (M+H)+.

Example 45

N-{3-chloro-4-[3-(1-methyl-1H-pyrazol-4-yl)-1H-indazol-6-yl]phenyl}-N'-(3-fluorophenyl)urea The title compound was prepared as described in Example 1, substituting 3-chloro-4-(4,4,5,5-tetramethyl-1,3,2-dioxaborolan-2-yl)aniline for 4-(4,4,5,5-tetramethyl-1,3,2-dioxaborolan-2-yl)aniline. $^1$H NMR (300 MHz, DMSO-d$_6$) δ ppm 3.94 (s, 3 H) 6.81 (dt, J=8.73, 2.78 Hz, 1 H) 7.18 (dt, J=9.52, 1.19 Hz, 2 H) 7.33 (dd, J=7.93, 7.14 Hz, 1 H) 7.43 (s 2 H) 7.50 (dt, J=11.9, 1.98 Hz, 1 H) 7.51 (s, 1 H) 7.85 (s, 1 H) 8.01 (s, 1H) 8.05 (d, J=8.33 Hz, 1 H) 8.38 (s, 1 H) 9.09 (s, 1 H) 9.11 (s, 1H) 13.00 (s, 1 H). MS (ESI(+)) m/e 461 (M+H)+.

Example 46

This example describes the assays that may be used to identify compounds having kinase activity.

To determine Aurora B activity of representative compounds of the invention, Active Aurora B enzyme (recombinant residues 1-344) and INCENP (recombinant GST fusion protein (Upstate)) were incubated in wells of a 384 well plate with biotinylted histone H3 peptide residues 1-21 (Upstate), 1 mM ATP, and various concentrations of inhibitors in a HEPES buffer, pH 7.4 containing MgCl$_2$, sodium othrovanadate, and Triton X-100. After 1 hour, the reaction was stopped with EDTA and anti-phospho-histone H3 Europium Cryptate (Cis-Bio) and SA-APC (Phycolink, Prozyme) were added to detect the phosphopeptide. The amount of phosphorylation was determined by the time-resolved fluorescence ratio of signals at 665 nm and 615 nm. The IC$_{50}$'s were calculated by an exponential fit of the inhibition values with the inhibitor concentrations using Assay Explorer software.

To determine Aurora A and C activity of representative compounds of the invention, Active Aurora A or C enzyme was incubated in wells of a 384 well plate with biotinylated STK substrate-2 (Upstate), 1 mM ATP, and various concentrations of inhibitors in a Hepes buffer, pH 7.4 containing MgCl$_2$, sodium othrovanadate, and Triton X-100. After 1 hour, the reaction was stopped with EDTA and anti-phospho-STK antibody Europium Cryptate (Upstate) and SA-XL665 (Upstate) were added to detect the phosphopeptide. The amount of phosphorylation was determined by the time-resolved fluorescence ratio of signals at 665 nm and 615 nm. The IC$_{50}$s were calculated by an exponential fit of the inhibition values with the inhibitor concentrations using Assay Explorer software.

To determine the activity of the various kinases, a homogenous time-resolved fluorescence (HTRF) in vitro kinase assay was used. (Mathis, G., HTRF(R) Technology. J Biomol Screen, 1999. 4(6): p. 309-314; Alfred J. Kolb, Paul V. Kaplita, David J. Hayes, Young-Whan Park, Christine Pernell, John S. Major and Gerard Mathis, *Drug Discovery Today*, 1998, 3, 333-342.)

For example for KDR, 7 ng/well of purified enzyme (His6-KDR 789-1354, MW 63 kD) was mixed with 0.5 μM N-biotinylated substrate (Biotin-Ahx-AEEEYFFLA-amide (SEQ. ID. 1)), various concentrations of inhibitor in reaction buffer (50 mM HEPES, pH 7.1, mM MgCl$_2$, 2 mM MnCl$_2$, 0.1% BSA and 1 mM DTT, 40 L final volume), ATP (1 mM final conc.) in a black 384-well plate. After 60 minutes incubation at room temperature, the reaction was quenched by addition of a buffered EDTA solution (final approximate concentrations: 30 mM EDTA, 0.1% BSA, 0.1% Triton X-100 and 0.24M KF) and a solution of revelation agents (to give 0.084 ng/well streptavidin-XL-665 (Cis-Bio) and 6.5 ng/well antiphsophotyrosine mAb PT66-K Europium kryptate) was added to the reaction mixture. The quenched reaction was allowed to stand at room temperature for 3 hours and was then read in a time-resolved fluorescence detector (InVision, Perkin-Elmer) at 620 nm and 665 nm sequentially with excitation. The ratio between the signal of 620 nm and 665 nm was used in the calculation of the IC$_{50}$.

To determine the induction of polyploidy in H1299 cells (Human Non-Small Cell Lung Carcinoma), NCI-H1299 were seeded (4K/well) into 96-well culture plates (tissue culture grade, black, flat-clear bottom) and incubated overnight to produce cell-to-plate adherance Inhibitors at varying concentrations were added into duplicate wells containing cells and culture media (RPMI 1640, 10% fetal calf serum) and incubated at 37 C for 48 hours. The plates were then washed with PBS and the adherent cells fixed by incubating with 3% formalin for 1 hour. After washing four times with PBS, the cells were then stained with Hoechst and subjected to fluorescent (3601/460e) microscopic high content analysis to determine the effect of inhibitors on nuclear size. Polyploid cells (>4N) were defined as those having nuclear area >750μ2. Potency was expressed as the concentration of inhibitor necessary to induce polyploidy in 15% of cells (EC15) and was calculated from least squares analysis of the log dose-response.

Table 1 and Table 2 demonstrate the utility of Examples 1-36 as inhibitors of multiple kinases.

TABLE 1

| Example | Aurora B IC$_{50}$ (µM) | Aurora A IC$_{50}$ (µM) | KDR IC$_{50}$ (µM) |
|---|---|---|---|
| 1 | 0.01915 | 0.37056 | 0.05485 |
| 2 | 0.01699 | >12.5 | 0.02742 |
| 3 | 0.04045 | 2.48866 | 0.04498 |
| 4 | 0.20737 | 1.46009 | 0.29094 |
| 5 | 0.19393 | >12.5 | 0.03166 |
| 6 | 0.02116 | 1.00285 | 0.08606 |
| 7 | >12.5 | >12.5 | 12.26343 |
| 8 | 0.02333 | 3.40187 | 0.52524 |
| 9 | 0.03267 | 0.22113 | 0.07635 |
| 10 | 0.02361 | 0.29394 | 0.05113 |
| 11 | 0.13573 | >12.5 | 0.02068 |
| 12 | 0.0441 | >12.5 | 0.06001 |
| 13 | 0.08637 | 10.90946 | 0.21693 |
| 14 | >12.5 | >12.5 | >12.5 |
| 15 | 0.1419 | >12.5 | 6.69077 |
| 16 | 0.01089 | >12.5 | 0.04463 |
| 17 | 1.32219 | >12.5 | 0.0488 |
| 18 | 0.15617 | >12.5 | 0.02374 |
| 19 | 0.10761 | 10.8006 | 0.04506 |
| 20 | 0.02472 | >12.5 | 0.12164 |
| 21 | 0.05826 | 10.23484 | 0.15372 |
| 22 | 0.03246 | 0.26656 | 0.01478 |
| 23 | 0.02488 | 0.24621 | 0.08073 |
| 24 | 1.02714 | >12.5 | >12.5 |
| 25 | 0.49336 | >12.5 | 0.03016 |
| 26 | 0.06229 | >12.5 | 0.32519 |
| 27 | 0.77345 | >12.5 | 0.0976 |
| 28 | 0.87108 | >12.5 | 0.03796 |
| 29 | 0.02498 | 3.33737 | 0.13671 |
| 30 | 0.01027 | 0.29923 | 0.03221 |
| 31 | 0.14197 | 5.20768 | 1.78816 |
| 32 | 1.92377 | >12.5 | 3.61315 |
| 33 | 0.11988 | >12.5 | 0.5838 |
| 34 | >12.5 | >12.5 | 0.27774 |
| 35 | 0.56942 | >12.5 | 0.55788 |
| 36 | >12.5 | >12.5 | 0.30336 |

TABLE 2

| Example | KDR cell IC$_{50}$ (µM) | Polyploid HCA IC$_{50}$ (µM) |
|---|---|---|
| 1 | 0.08708 | 0.001 |
| 2 | 0.04604 | 0.006 |
| 3 | 0.3157 | 0.035 |
| 6 | 0.18652 | 0.018 |
| 8 |  | 0.012 |
| 9 | 0.2999 | 0.014 |
| 10 | 0.20591 | 0.043 |
| 12 | 0.17589 | 0.055 |
| 16 | 0.13457 | 0.216 |
| 19 | 0.21632 |  |
| 20 |  | <0.001 |
| 21 |  | 0.128 |
| 22 | 0.04749 | 0.001 |
| 23 | 0.35459 | 0.01 |
| 26 |  | 0.013 |
| 29 |  | 0.113 |
| 30 | 0.12254 | 0.001 |

Compounds of the present invention assessed by the above-described assays were found to have kinase-inhibiting activity.

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:
1. A compound having Formula (I)

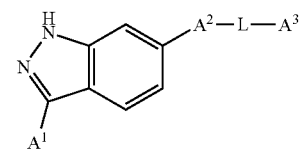

formula (I)

wherein
A$^1$ is aryl or heteroaryl, which is optionally substituted with one or more R$^1$,
R$^1$ is selected from the group consisting of R$^2$, alkyl, alkenyl, alkynyl, halogen, cyano, —OR$^3$, —C(O)R$^3$, —C(O)OR$^3$, —C(O)NR$^4$R$^5$, —OC(O)R$^3$, —NR$^4$R$^5$, —NR$^4$C(O)R$^5$, —NHC(O)NHR$^4$, —NHS(O)$_2$R$^3$, —SR$^3$, —S(O)R$^3$, —SO$_2$R$^3$, —SO$_2$NR$^4$R$^5$, —N$_3$, —NO$_2$, —CF$_3$, —CF$_2$CF$_3$, —OCF$_3$, and —OCF$_2$CF$_3$, wherein the R$^1$ alkyl, alkenyl, and alkynyl substituents are optionally substituted with one or more substituents selected from the group consisting of R$^6$, halogen, cyano, —OR$^3$, —C(O)R$^3$, —C(O)OR$^3$, —C(O)NR$^4$R$^5$, —OC(O)R$^3$, —NR$^4$R$^5$, and —NR$^4$C(O)R$^3$;
R$^2$ is aryl or heterocyclyl wherein the R$^2$ aryl and heterocyclyl substituents are optionally substituted with one or more substituents independently selected from the group consisting of R$^7$, halogen, cyano, —OR$^8$, —C(O)R$^8$, —C(O)OR$^8$, —C(O)NR$^9$R$^{10}$, —OC(O)R$^8$, —NR$^9$R$^{10}$, —NR$^9$C(O)R$^8$, —NHC(O)NHR$^9$, —NHS(O)$_2$R$^8$, —SR$^8$, —S(O)R$^8$, —SO$_2$R$^8$, —SO$_2$NR$^9$R$^{10}$, —N$_3$, —NO$_2$, —CF$_3$, —CF$_2$CF$_3$, —OCF$_3$, and —OCF$_2$CF$_3$;
R$^3$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;
R$^4$ and R$^5$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;
R$^6$ is aryl or heterocyclyl wherein the R$^6$ aryl and heterocyclyl substituents are optionally substituted with one or more substituents independently selected from the group consisting of R$^7$, halogen, cyano, —OR$^8$, —C(O)R$^8$, —C(O)OR$^8$, —C(O)NR$^9$R$^{10}$, —OC(O)R$^8$, —NR$^9$R$^{10}$, —NR$^9$C(O)R$^8$, —NHC(O)NHR$^9$, —NHS(O)$_2$R$^8$, —SR$^8$, —S(O)R$^8$, —SO$_2$R$^8$, —SO$_2$NR$^9$R$^{10}$, —N$_3$, —NO$_2$, —CF$_3$, —CF$_2$CF$_3$, —OCF$_3$, and —OCF$_2$CF$_3$;
R$^7$ is alkyl optionally substituted with one or more substituents selected from the group consisting of halogen, cyano, —OR$^{11}$, —C(O)R$^{11}$, —C(O)OR$^{11}$, —C(O)NR$^{12}$R$^{13}$, —OC(O)R$^{11}$, —NR$^{12}$R$^{13}$, —NR$^{12}$C(O)R$^{11}$, phenyl, and heterocycloalkyl;

$R^8$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^9$ and $R^{10}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^{11}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{12}$ and $R^{13}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$A^2$ is aryl or heteroaryl, which is optionally substituted with halogen;

L is $(CH_2)_mN(R^{14})C(O)N(R^{15})(CH_2)_n$, wherein m and n are independently 0 or 1; wherein $R^{14}$ and $R^{15}$ are independently selected from the group consisting of hydrogen and alkyl;

$A^3$ is aryl, cycloalkyl, cycloalkenyl, heterocyclyl, alkyl, alkenyl, or alkynyl, wherein (a) the $A^3$ alkyl, alkenyl, and alkynyl substituents are optionally substituted with one or more substituents selected from the group consisting of $R^{17}$, halogen, cyano, —$OR^{18}$, —$C(O)R^{18}$, —$C(O)OR^{18}$, —$C(O)NR^{19}R^{20}$, —$OC(O)R^{18}$, —$NR^{19}R^{20}$, —$NR^{19}C(O)R^{18}$, —$NHC(O)NHR^{19}$, —$NHS(O)_2R^{18}$, —$SR^{18}$, —$S(O)R^{18}$, —$SO_2R^{18}$, —$SO_2NR^{19}R^{20}$, —$N_3$, —$NO_2$, —$CF_3$, —$CF_2CF_3$, —$OCF_3$, and —$OCF_2CF_3$; (b) wherein the $A^3$ cycloalkyl, cycloalkenyl, aryl, and heterocyclyl substituents are optionally substituted with one or more $R^{16}$;

$R^{16}$ is selected from the group consisting of $R^{17}$, alkyl, alkenyl, alkynyl, halogen, cyano, —$OR^{21}$, —$C(O)R^{21}$, —$C(O)OR^{21}$, —$C(O)NR^{22}R^{23}$, —$OC(O)R^{21}$, —$NR^{22}R^{23}$, —$NR^{22}C(O)R^{21}$, —$NHC(O)NHR^{22}$, —$NHS(O)_2R^{21}$, —$SR^{21}$, —$S(O)R^{21}$, —$SO_2R^{21}$, —$SO_2NR^{22}R^{23}$, —$N_3$, —$NO_2$, —$CF_3$, —$CF_2CF_3$, —$OCF_3$; wherein the $R^{16}$ alkyl, alkenyl, and alkynyl substituents are optionally substituted with one or more substituents selected from the group consisting of aryl, heterocyclyl, cycloalkyl, halogen, cyano, —$OR^{21}$, —$C(O)R^{21}$, —$C(O)OR^{21}$, —$C(O)NR^{22}R^{23}$, —$NR^{22}R^{23}$, and —$NR^{22}C(O)R^{21}$;

$R^{17}$ is aryl or heterocyclyl wherein the $R^{17}$ aryl and heterocyclyl substituents are optionally substituted with one or more substituents independently selected from the group consisting of alkyl, alkenyl, alkynyl, halogen, cyano, —$OR^{24}$, —$C(O)R^{24}$, —$C(O)OR^{24}$, —$C(O)NR^{25}R^{26}$, —$OC(O)R^{24}$, —$NR^{25}R^{26}$, —$NR^{25}C(O)R^{26}$, —$NHC(O)NHR^{25}$, —$NHS(O)_2R^{24}$, —$SR^{24}$, —$S(O)R^{24}$, —$SO_2R^{24}$, —$SO_2NR^{25}R^{26}$, —$N_3$, —$NO_2$, —$CF_3$, —$CF_2CF_3$, —$OCF_3$;

$R^{18}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{19}$ and $R^{20}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^{21}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{22}$ and $R^{23}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^{24}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{25}$ and $R^{26}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

or a pharmaceutically acceptable salt thereof.

2. The compound according to claim 1, wherein $A^1$ is selected from the group consisting of phenyl, pyridyl, pyrimidinyl, pyridazinyl, pyrazyl, pyrrolyl, imidazyl, pyrazolyl, triazolyl, furanyl, thiophenyl, oxazolyl, isoxazolyl, thiazolyl, isothiazolyl, oxadiazolyl, and isothiazolyl.

3. The compound according to claim 1, wherein $A^1$ is selected from the group consisting of indolyl, isoindolyl, indazolyl, isoindazoyl, quinolinyl, benzoxazolyl, benzofuranyl, benzothiophenyl, benzothiazolyl, benzimidazolyl, benzotriazolyl, and 1,2,3,4-tetrahydroquinoline.

4. The compound according to claim 1, wherein $A^1$ is selected from the group consisting of

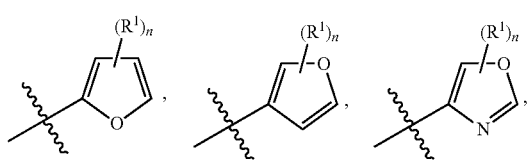

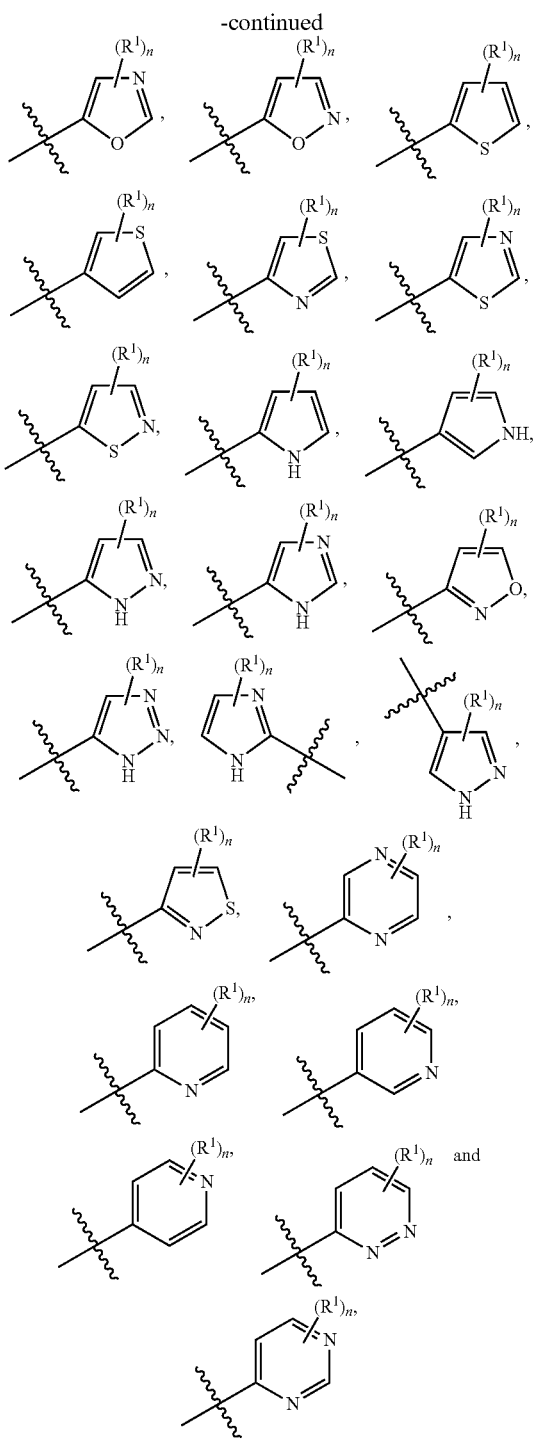

wherein n is 0, 1, or 2.

5. The compound according to claim 4
wherein $R^1$ is selected from the group consisting of $R^2$, alkyl, halogen, cyano, —$OR^3$, —$C(O)R^3$, —$C(O)OR^3$, —$C(O)NR^4R^5$, —$OC(O)R^3$, —$NR^4R^5$, —$NR^4C(O)R^5$, $CF_3$, $CF_2CF_3$, $OCF_3$, and $OCF_2CF_3$;

$R^2$ is phenyl;

$R^3$, at each occurrence, is independently selected from the group consisting of hydrogen and alkyl; and $R^4$ and $R^5$, at each occurrence, are independently selected from the group consisting of hydrogen and alkyl.

6. The compound according to claim 4 wherein n is 0.

7. The compound according to claim 1, wherein $A^1$ is selected from the group consisting of

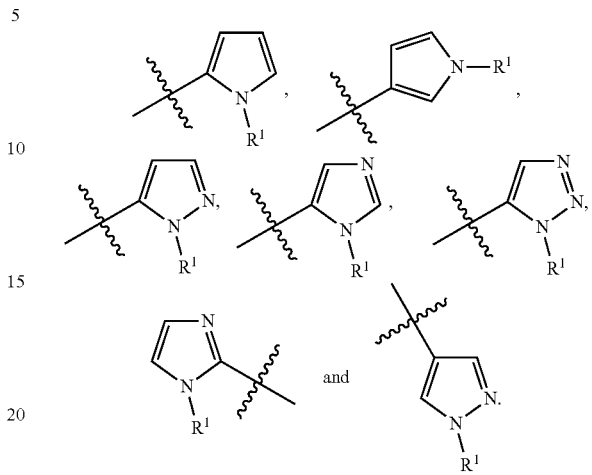

and

8. The compound according to claim 7, wherein $R^1$ is alkyl optionally substituted with 1 or 2 substituents selected from the group consisting of halogen, cyano, $OR^3$, $C(O)R^3$, $C(O)OR^3$, $NR^4R^5$, and $R^6$;

$R^3$, at each occurrence, is independently selected from the group consisting of hydrogen and alkyl;

$R^4$ and $R^5$, at each occurrence, are independently selected from the group consisting of hydrogen and alkyl;

$R^6$ is aryl or heterocyclyl wherein the $R^6$ aryl and heterocyclyl substituents are optionally substituted with one or more substituents independently selected from the group consisting of $R^7$, halogen, cyano, —$OR^8$, —$C(O)R^8$, —$C(O)OR^8$, —$NR^9R^{10}$, —$NR^9C(O)R^8$, —$C(O)NR^9R^{10}$;

$R^7$ is alkyl optionally substituted with one or more substituents selected from the group consisting of halogen, cyano, —$OR^{11}$, —$C(O)R^{11}$, —$C(O)OR^{11}$, —$C(O)NR^{12}R^{13}$, —$NR^{12}R^{13}$, and —$NR^{12}C(O)R^{11}$;

$R^8$, at each occurrence, is independently selected from the group consisting of hydrogen and alkyl;

$R^9$ and $R^{10}$, at each occurrence, are independently selected from the group consisting of hydrogen and alkyl;

$R^{11}$, at each occurrence, is independently selected from the group consisting of hydrogen and alkyl; and $R^{12}$ and $R^{13}$, at each occurrence, are independently selected from the group consisting of hydrogen and alkyl.

9. The compound according to claim 8, wherein R is methyl, ethyl, n-propyl, iso-propyl, n-butyl, sec-butyl, or n-pentyl.

10. The compound according to claim 8, wherein $R^1$ is $CH_2R^{27}$, $CH_2CH_2R^{27}$, or $H_2CH_2CH_2R^{27}$;

$R^{27}$ is selected from the group consisting of halogen, cyano, hydroxyl, —$OC_{1-4}$-alkyl, —$C(O)OH$, —$C(O)OC_{1-4}$-alkyl, —$C(O)NH_2$, —$C(O)NHC_{1-4}$-alkyl, and —$C(O)N(C_{1-4}$-alkyl$)_2$, and wherein $C_{1-4}$-alkyl is an unsubstituted branched or straight chain alkyl group.

11. The compound according to claim 8, wherein $R^1$ is $CH_2R^{28}$, $CH_2CH_2R^{28}$, or $CH_2CH_2CH_2R^{28}$;

$R^{28}$ is selected from the group consisting of piperidinyl, piperazinyl, morpholino, tetrahydrofuranyl, pyrrolidinyl, 3-oxo-1-piperazinyl, 2-oxo-1-pyrrolidinyl, imidazolyl, pyridinyl, and 2-oxo-1-imidazolidinyl, wherein $R^{24}$ is optionally substituted with —$C_{1-4}$-alkyl, halogen, cyano, hydroxyl, —$OC_{1-4}$-alkyl, —C(O)OH, —C(O)O$C_{1-4}$-alkyl, —C(O)$C_{1-4}$-alkyl, —C(O)NH$_2$, —C(O)NH$C_{1-4}$-alkyl, and —C(O)N($C_{1-4}$-alkyl)$_2$, and wherein $C_{1-4}$-alkyl is an unsubstituted branched or straight chain alkyl group.

12. The compound according to claim 7, wherein $R^1$ is $R^2$, and wherein $R^2$ is phenyl or heterocycloalkyl.

13. The compound according to claim 12, wherein $R^2$ is selected from the group consisting of piperidinyl, piperazinyl, morpholino, tetrahydrofuranyl, pyrrolidinyl, 3-oxo-1-piperazinyl, 2-oxo-1-pyrrolidinyl, imidazolyl, pyridinyl, and 2-oxo-1-imidazolidinyl, wherein $R^2$ is optionally substituted with —$C_{1-4}$-alkyl, halogen, cyano, hydroxyl, —$OC_{1-4}$-alkyl, —C(O)OH, —C(O)O$C_{1-4}$-alkyl, —C(O)$C_{1-4}$-alkyl, —C(O)NH$_2$, —C(O)NH$C_{1-4}$-alkyl, and —C(O)N($C_{1-4}$-alkyl)$_2$, and wherein $C_{1-4}$-alkyl is an unsubstituted branched or straight chain alkyl group.

14. The compound according to claim 1, wherein $A^2$ is phenyl.

15. The compound according to claim 1, wherein L is —NHC(O)NH—.

16. The compound according to claim 1, wherein $A^3$ is selected from the group consisting of phenyl, naphthalenyl, tetrahydronaphthalenyl, cyclopentyl, cyclopentenyl, cyclohexyl, cyclohexenyl, furanyl, pyridyl, and thiophenyl.

17. The compound according to claim 16, wherein $A^3$ is phenyl which is optionally substituted with 1, 2, or 3 $R^{16}$, wherein $R^{16}$ is selected from the group consisting of —$CH_3$, —$CH_2CH_3$, fluoro, chloro, bromo, cyano, —$NO_2$, —$OCH_3$, —$OCH_2CH_3$, —$CF_3$, —$CF_2CF_3$, —$OCF_3$, —$OCF_2CF_3$, —$NH_2$, —$N(CH_3)_2$, —OH, —OPh, —C(=O)$CH_3$, —C(=O)$CH_2CH_3$, and C(=O)OH.

18. The compound according to claim 1, wherein $A^3$ is alkyl and $R^{10}$ is alkyl.

19. The compound according to claim 1, having formula (II)

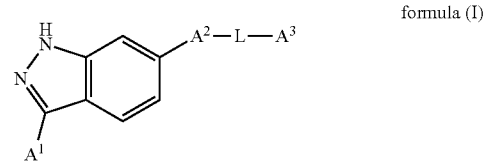

formula (II)

wherein $A^1$ and $A^3$ are as defined in claim 1.

20. The compound according to claim 19, wherein $A^1$ is selected from the group consisting of

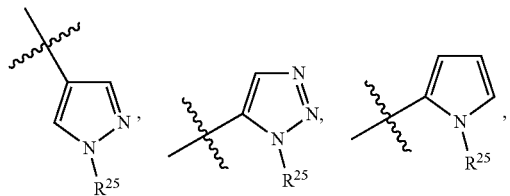

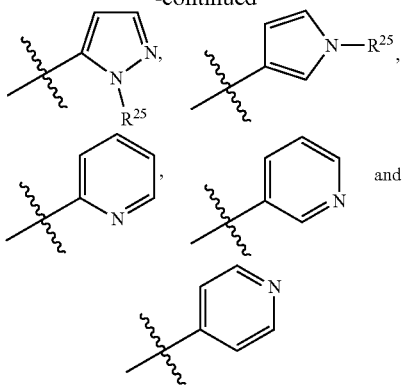

wherein $R^{25}$ is hydrogen or alkyl, wherein the alkyl is optionally substituted with hydroxyl, —$OC_{1-4}$-alkyl, —C(O)OH, or —C(O)O$C_{1-4}$-alkyl.

21. The compound according to claim 19, wherein $A^3$ is phenyl, wherein the phenyl is optionally substituted with —$CH_3$, —$CH_2CH_3$, fluoro, chloro, —$OCH_3$, —$OCH_2CH_3$, —$CF_3$, —$CF_2CF_3$, —$OCF_3$, and —$OCF_2CF_3$.

22. A compound having formula (I),

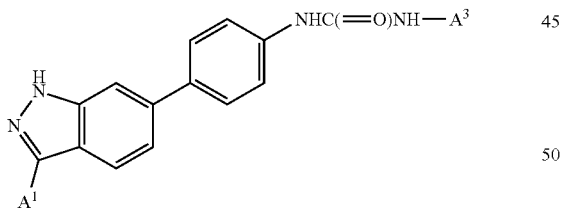

formula (I)

wherein $A^1$ is aryl or heteroaryl, which is optionally substituted with one or more $R^1$, $R^1$ is selected from the group consisting of $R^2$, alkyl, alkenyl, alkynyl, halogen, cyano, —$OR^3$, —C(O)$R^3$, —C(O)$OR^3$, —C(O)$NR^4R^5$, —OC(O)$R^3$, —$NR^4R^5$, —$NR^4C(O)R^5$, —NHC(O)$NHR^4$, —NHS(O)$_2R^3$, —$SR^3$, —S(O)$R^3$, —SO$_2R^3$, —SO$_2NR^4R^5$, —$N_3$, —$NO_2$, —$CF_3$, —$CF_2CF_3$, —$OCF_3$, and —$OCF_2CF_3$, wherein the $R^1$ alkyl, alkenyl, and alkynyl substituents are optionally substituted with one or more substituents selected from the group consisting of $R^6$, halogen, cyano, —$OR^3$, —C(O)$R^3$, —C(O)$OR^3$, —C(O)$NR^4R^5$, —OC(O)$R^3$, —$NR^4R^5$, and —$NR^4C(O)R^3$;

$R^2$ is aryl or heterocyclyl wherein the $R^2$ aryl and heterocyclyl substituents are optionally substituted with one or more substituents independently selected from the group consisting of $R^7$, halogen, cyano, —$OR^8$, —C(O)$R^8$, —C(O)$OR^8$, —C(O)$NR^9R^{10}$, —OC(O)$R^8$, —$NR^9R^{10}$, —$NR^9C(O)R^8$, —NHC(O)$NHR^9$, —NHS(O)$_2R^8$, —$SR^8$, —S(O)$R^8$, —SO$_2R^8$, —SO$_2NR^9R^{10}$, —$N_3$, —$NO_2$, —$CF_3$, —$CF_2CF_3$, —$OCF_3$, and —$OCF_2CF_3$;

$R^3$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^4$ and $R^5$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^6$ is aryl or heterocyclyl wherein the $R^6$ aryl and heterocyclyl substituents are optionally substituted with one or more substituents independently selected from the group consisting of $R^2$, halogen, cyano, —$OR^8$, —$C(O)R^8$, —$C(O)OR^8$, —$OC(O)R^8$, —$NR^9R^{10}$, —$NR^9C(O)R^8$, —$NHC(O)NHR^9$, —$C(O)NR^9R^{10}$, —$SR^8$, —$S(O)R^8$, —$SO_2R^8$, —$OC(O)OR^8$, —$SO_2NR^9R^{10}$, —$N_3$, —$NO_2$, —$CF_3$, —$CF_2CF_3$, —$OCF_3$, and —$OCF_2CF_3$;

$R^7$ is alkyl optionally substituted with one or more substituents selected from the group consisting of halogen, cyano, —$OR^{11}$, —$C(O)R^{11}$, —$C(O)OR^{11}$, —$C(O)NR^{12}R^{13}$, —$OC(O)R^{11}$, —$NR^{12}R^{13}$, —$NR^{12}C(O)R^{11}$, phenyl, and heterocycloalkyl;

$R^8$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^9$ and $R^{10}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^{11}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{12}$ and $R^{13}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$A^2$ is

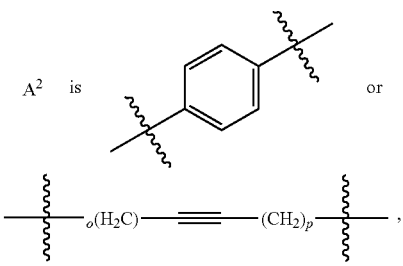

wherein o and p are each independently 0, 1, or 2;

L is —$(CH_2)_mN(R^{14})C(O)$—, —$C(O)N(R^{15})(CH_2)_n$—, or —$(CH_2)_mN(R^{14})C(O)N(R^{15})(CH_2)_n$—, wherein m and n are independently 0 or 1; wherein $R^{14}$ and $R^{15}$ are independently selected from the group consisting of hydrogen and alkyl;

$A^3$ is aryl, cycloalkyl, cycloalkenyl, heterocyclyl, alkyl, alkenyl, or alkynyl, wherein (a) the $A^3$ alkyl, alkenyl, and alkynyl substituents are optionally substituted with one or more substituents selected from the group consisting of $R^{17}$, halogen, cyano, —$OR^{18}$, —$C(O)R^{18}$, —$C(O)OR^{18}$, —$OC(O)R^{18}$, —$NR^{19}R^{20}$, —$NR^{19}C(O)R^{18}$, —$NHC(O)NHR^{20}$, —$C(O)NR^{19}R^{20}$, —$SR^{18}$, —$S(O)R^{18}$, —$SO_2$, —$OC(O)OR^{18}$, —$SO_2NR^{19}R^{20}$, —$N_3$, —$NO_2$, —$CF_3$, —$CF_2CF_3$, —$OCF_3$, and —$OCF_2CF_3$; (b) wherein the $A^3$ cycloalkyl, cycloalkenyl, aryl, and heterocyclyl substituents are optionally substituted with one or more $R^{16}$;

$R^{16}$ is selected from the group consisting of $R^{17}$, alkyl, alkenyl, alkynyl, halogen, cyano, —$OR^{21}$, —$C(O)R^{21}$, —$C(O)OR^{21}$, —$OC(O)R^{21}$, —$NR^{22}R^{23}$, —$NR^{22}C(O)R^{21}$, —$NHC(O)NHR^{22}$, —$C(O)NR^{22}R^{23}$, —$SR^{21}$, —$S(O)R^{21}$, —$SO_2R^{21}$, —$OC(O)OR^{21}$, —$SO_2NR^{22}R^{23}$, —$N_3$, —$NO_2$, —$CF_3$, —$CF_2CF_3$, —$OCF_3$; wherein the $R^{16}$ alkyl, alkenyl, and alkynyl substituents are optionally substituted with one or more substituents selected from the group consisting of aryl, heterocyclyl, cycloalkyl, halogen, cyano, —$OR^{21}$, —$C(O)R^{21}$, —$C(O)OR^{21}$, —$C(O)NR^{22}R^{23}$, —$OC(O)R^{21}$, —$NR^{22}R^{23}$, and —$NR^{22}C(O)R^{21}$;

$R^{17}$ is aryl or heterocyclyl wherein the $R^{17}$ aryl and heterocyclyl substituents are optionally substituted with one or more substituents independently selected from the group consisting of alkyl, alkenyl, alkynyl, halogen, cyano, —$OR^{21}$, —$C(O)R^{21}$, —$C(O)OR^{21}$, —$OC(O)R^{21}$, —$NR^{22}R^{23}$, —$NR^{22}C(O)R^{21}$, —$NHC(O)NHR^{22}$, —$C(O)NR^{22}R^{23}$, —$SR^{21}$, —$S(O)R^{21}$, —$SO_2R^{21}$, —$OC(O)OR^{21}$, —$SO_2NR^{22}R^{23}$, —$N_3$, —$NO_2$, —$CF_3$, —$CF_2CF_3$, —$OCF_3$;

$R^{18}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{19}$ and $R^{20}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

$R^{21}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of hydroxyl, halogen, and cyano;

$R^{22}$ and $R^{23}$, at each occurrence, are independently selected from the group consisting of hydrogen, alkyl, alkenyl, alkynyl, aryl, heterocyclyl, and cycloalkyl, wherein the alkyl, alkenyl, alkynyl, heterocyclyl, and cycloalkyl are optionally substituted with one or more substituents independently selected from the group consisting of hydroxyl, halogen, and cyano;

or a pharmaceutically acceptable salt thereof.

23. A pharmaceutical composition comprising a compound or pharmaceutically acceptable salt of claim 1 and pharmaceutically acceptable excipient.

* * * * *

UNITED STATES PATENT AND TRADEMARK OFFICE
CERTIFICATE OF CORRECTION

PATENT NO. : 8,293,738 B2  Page 1 of 1
APPLICATION NO. : 13/106189
DATED : October 23, 2012
INVENTOR(S) : Michaelides et al.

It is certified that error appears in the above-identified patent and that said Letters Patent is hereby corrected as shown below:

In the Claims:

Column 58, line 52, claim 9: "wherein R is" to read as --wherein $R^1$ is--

Column 62, line 08, claim 22: "-$SO_2$," to read as -- -$SO_2R^{18}$,--

Signed and Sealed this
Sixteenth Day of September, 2014

Michelle K. Lee
*Deputy Director of the United States Patent and Trademark Office*